(12) United States Patent
Stahl

(10) Patent No.: US 6,787,167 B1
(45) Date of Patent: Sep. 7, 2004

(54) USE OF NATURAL VEGETABLE COMPONENTS AS FLAVORING AGENTS IN CHEWING GUM COATINGS

(75) Inventor: Bronislaw-Jan Stahl, Vejle (DK)

(73) Assignee: Dandy A/S, Vejle (DK)

( * ) Notice: Subject to any disclaimer, the term of this patent is extended or adjusted under 35 U.S.C. 154(b) by 0 days.

(21) Appl. No.: 09/856,540

(22) PCT Filed: Nov. 23, 1999

(86) PCT No.: PCT/DK99/00649

§ 371 (c)(1),
(2), (4) Date: Jun. 26, 2001

(87) PCT Pub. No.: WO00/30465

PCT Pub. Date: Jun. 2, 2000

(30) Foreign Application Priority Data

Nov. 23, 1998 (DK) ........................ 1998 01540

(51) Int. Cl.⁷ ................................ A23G 3/30
(52) U.S. Cl. ........................................ 426/5
(58) Field of Search ............................. 426/5

(56) References Cited

U.S. PATENT DOCUMENTS

| | | | |
|---|---|---|---|
| 3,632,358 A | | 1/1972 | Echeandia et al. |
| 3,795,744 A | | 3/1974 | Ogawa et al. |
| 3,962,463 A | * | 6/1976 | Witzel ........................ 426/5 |
| 4,250,195 A | | 2/1981 | Cherukuri et al. |
| 4,317,838 A | | 3/1982 | Cherukuri et al. |
| 4,385,071 A | | 5/1983 | Yakimischak |

FOREIGN PATENT DOCUMENTS

| | | |
|---|---|---|
| CA | 2027177 | 4/1991 |
| EP | 0314626 | 5/1989 |
| EP | 0531692 B1 | 3/1993 |
| FR | 2652720 | 12/1991 |
| GB | 711187 | 6/1954 |
| WO | 90/00018 | 1/1990 |
| WO | WO 90/06689 | 6/1990 |
| WO | 0 414 932 A1 | 3/1991 |
| WO | 2652720 | 4/1991 |
| WO | 0 426 428 A1 | 5/1991 |
| WO | WO 93/09678 | 5/1993 |
| WO | 94/01002 | 1/1994 |
| WO | 94/13152 | 6/1994 |
| WO | 95/00038 | 1/1995 |
| WO | 95/27402 | 10/1995 |
| WO | 0 717 986 A1 | 6/1996 |

OTHER PUBLICATIONS

EP—Standard Search Report in PA 1998 01540, Nov. 23, 1998, DK.

* cited by examiner

Primary Examiner—Arthur L. Corbin
(74) Attorney, Agent, or Firm—Hunton & Williams LLP

(57) ABSTRACT

The present invention relates to the use or natural vegetable flavouring components as flavouring agents in chewing gum coating. The addition of a natural vegetable component to a chewing gum coating results in increased flavour sensation. The invention also relates to a method for the preparation of a chewing gum wherein the coating comprises a natural vegetable component as flavouring agent. The chewing gum comprises a) an insoluble gum base; b) a water soluble portion; c) a coating comprising a flavouring agent wherein at least 10% by weight of the flavouring agent is a natural vegetable flavouring agent comprising plant cellular material.

43 Claims, 12 Drawing Sheets

USE OF NATURAL VEGETABLE COMPONENTS AS FLAVORING AGENTS IN CHEWING GUM COATINGS

The present invention relates to the use of natural vegetable flavouring components as flavouring agents in chewing gum coating.

According to the present invention it has surprisingly been found that addition of a natural vegetable component to a chewing gum coating results in increased flavour sensation. The invention also relates to a method for the preparation of a chewing gum wherein the coating comprises a natural vegetable component as flavouring agent.

The aroma agents and flavours generally used in chewing gum coating are for instance natural and synthetic flavourings in the form of essential oils, essences, and extracts. The flavours may be in the form of liquids or powders. The powders are normally prepared on the basis on liquid essences or extracts.

Natural flavours are commonly subject to deterioration due to heat treatment, contact with air, light and moisture. In addition, natural flavours may due to the preparation method lack the natural taste sensation because many taste notes of the original product are changed or disappears during the processes. Accordingly, the overall taste sensation is changed.

Patent application CA 2,027,177 discloses use of fruit juice concentrate as a agent.

U.S. Pat. No. 3,632,358 relates to the use of particles of freeze-dried food in the chewing gum formulations prepared from a chewing gum vehicle. The freeze-dried particles are added to the water-soluble portion of the formulation. The chewing gum is not coated.

BRIEF DESCRIPTION OF THE INVENTION

According to the present invention, it has surprisingly been found that natural flavour sources such as dried fruits or other vegetable material in its natural form or dried form are excellent flavours in chewing gum coatings. The natural dried fruits or other vegetable material are useful flavours and is used in the coating of the chewing gum. In a further embodiment, the natural dried fruits or other vegetable material may also be added to the chewing gum formulation in order to keep the good taste sensation initiated by use of the dried fruits or other vegetable material in the coating.

It is believed that the surprising effect of the natural vegetable flavouring component according to the present invention is not only due to a minimal treatment of the natural vegetable flavouring agent but is also related to the content of cellular material from the plant. The cellular material may serve as reservoir for the flavouring components and may also help to preserve the sensible chemical structure of the natural selection of flavouring components. When both a great part of the flavouring components are retained as well as in the natural ratios, a very natural taste sensation is obtained. In addition, by being released during the chewing period of a chewing gum where saliva solubilize the different taste components in a way which is very similar to the normal chewing of e.g. a fruit, the consumer experience a much more natural taste sensation than may be obtained by conventional flavours including flavours prepared on the basis of natural products such as from juices. Accordingly, in a preferred embodiment the natural vegetable-flavouring agent of the present invention comprises more or less intact cellular components.

Flavour powders known in the art are conventionally prepared by spray drying of aqueous solutions essences or extracts and drying with hot air. However, during the process the flavour looses the characteristics of the natural taste the liquid flavour might have initially, the liquid may already have lost a great part of the full taste sensation of the original product as liquid flavour lack the full taste characteristics of the original product.

Furthermore, the taste sensation during the compete chewing process is of great importance for the customer. It has now surprisingly been found that use of a dried natural flavouring agent according to the present invention may improve the taste sensation of a chewing gum wherein the dried fruits or other vegetable material is used as flavours in the coating. With relative small amounts of freeze dried natural vegetable flavouring components the following improved characteristics has been identified: less perfumed taste, less synthetic taste, less astringent sensation, increased intensity, increased impact, increased sourness and freshness.

In addition to the increase in taste sensation the use of the natural flavouring components also results in the chewing gum wherein synthetic colouring agents can by avoided. In a preferred embodiment, the natural flavouring component is used in the dragée layer as well as in the chewing gum resulting in an excellent taste as well as colour of the chewing gum product.

Use of the dried natural vegetable components according to the present invention may cause difficulties in a conventional coating process using a wet coating suspension. Accordingly, the present invention also relates to a coating process wherein the dried natural vegetable flavouring agent is applied to the coating in dry form.

Examples natural vegetable flavouring agents according to the present invention are preferable fruits and herbs and include coconut, grape fruit, orange, lime, lemon, mandarin, pineapple, strawberry, raspberry, tropical fruits such as mango, passion fruit, kiwi; apple, pear, peach, strawberry, apricot, raspberry, cherry, pineapple, grapes, banana, cranberry, blueberry, black current, red current, gooseberry, and lingon berries. The herbs include thyme, basil, camille, valerian, fennel, parsley, camomile, tarragon, lavender, dill, cumin, bergamot, salvia, aloe vera and balsam. Also aromatic vegetables such as tomatoes may be used according to the present invention.

In a preferred embodiment of the invention, plants known as menthol, spearmint, peppermint, and eucalyptus are used as flavouring agents according to the invention.

The vegetable flavouring component agent may include al parts of the plant, however, the most aromatic part are preferred such as e.g. the leaves of the eucalyptus, spearmint, peppermint and will be known by the skilled person.

As is well known in the art, chewing gum comprises an insoluble gum part and a water-soluble part. The Standard gum bases generally contain elastomers, resins, fats, oils, waxes, emulsifiers and inorganic fillers.

Thus, the invention relates to a coated chewing gum comprising a core of chewing gum and a coating that comprises a coating material, and one or more dried natural vegetable components as flavours.

In one embodiment, the invention relates to a method for the preparation of a coated chewing gum according to the invention comprising the following steps:

1) preparation of a core of chewing gum in a manner known per se,
2) preparation of a coating suspension, also in a manner known per se, 3) repeated applications of the coating suspension onto the cores of chewing gum also in a manner known per se, preferable at a temperature in the interval 30–90° C., preferably 35–75° C.,
4) Applying on the coating the dried vegetable flavouring agent in dried form in one or more increment(s) after the application of the coating suspension, and optionally repeating step 3) and 4)
5) optionally, application of one or more flavours in liquid form in one or more increments between the applications of the coating suspension,
6) optionally, finally application of a surface layer.

Applying of the solid natural flavour agent preferable performed without drying of the coating suspension in order to enable adherence of a substantial amount of the dried flavour to the coating. The drying time for the coating suspension depends on the specific coating formulation, however, the dried flavour is added to the coated chewing gum substantially without delay after the coating processes are finished. If desired, the coated chewing gum may be wetted in case the coating has been allowed to dry for too long time whereby the coated chewing gum is no longer sticky.

The coating process may be repeated as many times as needed in order to obtain the desired thickness of the coating. It is also within the present invention to use different flavours in the same coating layer or use one active substance in one layer, and a second active substance in another layer.

As the flavour is located in the outer part of the coating, the active substance(s) is/are exposed to the consumer within a short period of chewing. Accordingly, in a further embodiment, the invention relates to the use of one or more natural vegetable flavours in dried form in the coating of a coated chewing gum in order to obtain a fast onset of the effect.

DETAILED DESCRIPTION OF THE INVENTION

The present invention relates to a chewing gum comprising
a) an insoluble gum base;
b) a water soluble portion;
c) a coating comprising a flavouring agent wherein at least 10% by weight of the flavouring agent in the coating is a natural vegetable flavouring agent. Preferable, the coating comprises a flavouring agent wherein at least 20% by weight such as at least 30% by weight preferable as at least 40%, more preferred at least 50%, still more preferred at least 60% by weight of the flavouring agent is a natural vegetable flavouring agent.

In most cases at least at 70% by weight such as at least 80%, preferable at least 90%, more preferred at least 95% by weight of the flavouring agent in the coating is natural vegetable flavouring agent.

In addition, the only flavouring agent used in the coating may be a natural vegetable flavouring agent.

The natural vegetable flavouring agent in the coating may be selected from coconut, grape fruit, orange, lime, lemon, mandarin, pineapple, strawberry, raspberry, mango, passion fruit, kiwi, apple, pear, peach, strawberry, apricot, raspberry, cherry, pineapple, grapes, banana, cranberry, blueberry, black current, red current, gooseberry, and lingon berries, thyme, basil, camille, valerian, fennel, parsley, camomile, tarragon, lavender, dill, cumin, bergamot, salvia, aloe vera balsam, spearmint, peppermint, eucalyptus and mixtures thereof. It is preferred that the natural flavouring agent in the coating is dried in order to obtain sufficient taste.

Accordingly, the water content of the natural flavouring agent in the coating is less than 75% by weight, such as less than 60%, preferable less than 40%, more preferred less than 30%, such as less than 25%. Even drier flavours are preferred such as a water content of the natural flavouring agent in the coating of less than 20% by weight, such as less than 15%, more preferred less than 10% such as between 1.5–7%, more preferred between 2–6%. This may be obtained by freeze-drying.

The dried natural flavouring agent in the coating may be in the form of a powder, slices or pieces of combinations thereof and the particle size may be less than 3 mm, such as less than 2 mm, more preferred less than 1 mm, calculated as the longest. dimension of the particle. Even smaller particles may be obtained such as coatings wherein the natural flavouring agent in the coating is in a form where the particle size is from about $3\mu$ to 2 mm, such as from $4\mu$ to 1 mm.

Some fruits comprises very tasteful seeds, accordingly, the flavouring agent in the coating may comprise seeds from a fruit e.g. from strawberry, blackberry and raspberry, and which seeds are substantially intact.

By use of the natural flavour according to the invention a natural colour may also be obtained. Both as a basic colour but also spots of colour from larger particle size may obtained 22. A method for preparing a chewing gum composition comprising providing a mixture of
a) an insoluble gum base; and
b) a water soluble portion;
c) forming chewing gum pieces
d) coating the chewing gum pieces with a coating comprising a flavouring agent wherein at least 10% by weight of the flavouring agent is a natural vegetable flavouring agent.

The gum base may be any conventional and includes s wherein the chewing gum base contains about 5 weight-% to 50 weight-% elastomer which may be of natural or more preferred of synthetic origin, about 5 to about 55 weight-% elastomer plasticizer, about 0 to 50 weight-%. filler, about 5 to about 35 weight-% softener, and optional minor amounts (about 1% or less) of miscellaneous ingredient such as antioxidants, colorants, etc.

According to the present text, the term softener is used for ingredients, which soften the gum or chewing gum formulation and encompass wax, fax, oil, emulsifiers, surfactants, solubilizers etc.

The gum base used in the chewing gum according to the invention is generally prepared in a conventional manner by heating and mixing the different ingredients such as elastomers, resins, inorganic fillers, waxes, fats, and emulsifiers etc.

The insoluble gum base generally comprises fats and oils, resins, elastomers, softeners, and inorganic fillers. The gum base may or may not include wax. The insoluble gum base can constitute approximately 5 to about 95 percent, by weight, of the chewing gum, more commonly, the gum base constitutes 10 to about 50 percent of the gum, and in a preferred embodiment, 20 to about 35 percent, by weight, of the chewing gum.

Synthetic elastomers may include, but are not limited to, polyisobutylene with a GPC weight average molecular weight of about 10,000 to about 95,000, isobutylene-isoprene copolymer (butyl elastomer), styrene-butadiene copolymers having styrene-butadiene ratios of about 1:3 to about 3:1, polyvinyl acetate having a GPC weight average molecular weight of about 2,000 to about 90,000, polyisoprene, polyethylene, vinyl acetate-vinyl laurate copolymer having vinyl laurate content of about 5 to about 50 percent by weight of the copolymer, and combinations thereof. Preferred ranges are, for polyisobutylene, 50,000 to 80,000 GPC weight average molecular weight, for styrene-butadiene, 1:1 to 1:3 bound styrene-butadiene, for polyvinyl acetate, 3,000 to 80,000 GPC weight average molecular weight with the higher molecular weight polyvinyl acetates typically used in bubble gum base, and for vinyl acetate-vinyl laurate, vinyl laurate content of 10–45 percent.

Natural elastomers may include natural rubber such as smoked or liquid latex and guayule as well as natural gums such as jelutong, lechi caspi, massaranduba balata, sorva, perillo, rosindinha, massaranduba chocolate, chicle, nispero, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, massaranduba balata and sorva.

Elastomers plasticizers may include, but are not limited to, natural rosin esters, often called estergums, such as glycerol esters of partially hydrogenated rosin, glycerol esters polymerized rosin, glycerol esters of partially dimerized rosin, glycerol esters of rosin, pentaerythritol esters of partially hydrogenated rosin, methyl and partially hydrogenated methyl estersof rosin, pentaerythritol esters of rosin; synthetics such as terpene resins derived from alpha-pinene, beta-pinene, and/or d-limonene; and any suitable combinations of the foregoing. The preferred elastomer will also vary depending on the specific application, and on the type of elastomer which is used. Fillers/texturizers may include magnesium and calcium carbonate, ground limestone, silicate types such as magnesium and aluminium silicate, clay, alumina, talc, titanium oxide, mono-, di- and tri-calcium phosphate, cellulose polymers, such as wood, and combinations thereof.

In an embodiment of the invention softeners/emulsifiers may include tallow, hydrogenated tallow, hydrogenated and partially hydrogenated vegetable oils, cocoa butter, glycerol monostearate, glycerol triacetate, lechithin, mono-, di- and triglycerides, acetylated monoglycerides, fatty acids (e.g. stearic, palmitic, oleic and linoleic acids), and combinations thereof.

According to a further embodiment of the invention, sucrose fatty acid esters are used for increasing the flavour properties of the chewing gum formulations.

In addition to the natural flavour agent according to the invention, the chewing gum formulation may comprise conventional flavours. The aroma agents and flavours usable for the compositions according to the present invention are for instance natural and synthetic flavourings (including nature identical flavourings) in the form of essential oils, essences, extracts, powders, including acids and other substances capable of affecting the taste profile. Examples of liquid and powdered flavourings include coconut, coffee, chocolate, vanilla, grape fruit, orange, lime, menthol, liquorice, caramel aroma, honey aroma, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

In addition to the natural vegetable flavouring agents according to the present invention, various synthetic flavours may also be used if desired. The conventional aroma agents and/or flavours may be used in an amount of from 0.01 to about 30 weight-% of the final product depending on the intensity of the aroma and/or flavour used. Preferably, the content of aroma/flavour is in the range of from 0.2 to 3% of the total composition.

Colorants and whiteners may include FD&C-type dyes and lakes, fruit and vegetable extracts, titanium dioxide, and combinations thereof.

The base may or may not include wax. Waxes may include synthetic waxes such as microcrystalline or paraffin waxes, or natural waxes such as carnauba, beeswax, candellila, or polyethylene wax.

In addition to a water insoluble gum base portion, a typical chewing gum composition includes a water soluble bulk portion. The water soluble portion can include bulk sweeteners, high intensity sweeteners, flavouring agents, softeners, emulsifiers, colours, acidulants, fillers, antioxidants, and other components that provide desired attributes.

The softeners, which are also known as plasticizers and plasticizing agents, generally constitute between approximately 0.5 to about 15% by weight of the chewing gum. The softeners may, in addition to including sucrose polyesters, include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute 5 to about 95% by weight of the chewing gum, more typically constitute 20 to about 80% by weight, and more commonly, 30 to 60% by weight of the gum.

Sugar sweeteners generally include saccharide-containing components commonly known in the chewing gum art, but not limited to, sucrose, dextrose, maltose, dextrin, dried invert sugar, fructose, levulose, galactose, corn syrup solids, and the like, alone or in combination.

Sorbitol can be used as a sugarless sweetener. Additionally, sugarless sweeteners can include, but are not limited to, other sugar alcohols such as mannitol, xylitol, hydrogenated starch hydrolysates, maltitol, and the like, alone or in combination. High intensity artificial sweeteners can also be used in combination with the above. Preferred sweeteners include, but are not limited to sucralose, aspartame, salts of acesulfame, alitame, saccharin and its salts, cyclamic acid and its salts, glycyrrhizin, dihydrochalcones, thaumatin, monellin, and the like, alone or in combination. In order to provide longer lasting sweetness and flavour perception, it may be desirable to encapsulate or otherwise control the release of at least a portion of the artificial sweetener. Such techniques as wet granulation, wax granulation, spray drying, spray chilling, fluid bed coating, coacervation, and fiber extrusion may be used to achieve the desired release characteristics.

Usage level of the artificial sweetener will vary greatly and will depend on such factors as potency of the sweetener, rate of release, desired sweetness of the product, level and type of flavour used and cost considerations. Thus, the active level of artificial sweetener may vary from 0.02 to about 8%. When carriers used for encapsulation are included, the usage level of the encapsulated sweetener will be proportionately higher.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include polydextrose; Raftilose, Raftilin; Fructooligosaccharides (NutraFlora); Palatinose oligosaccharide; Guar Gum Hydrolysate (Sun Fiber); or indigestible dextrin (Fibersol). However, other low calorie bulking agent can be used.

Any of the usual elastomers can be used in a quantity of typically 5–50 weight-%. The elastomer may be of natural origin, for instance such as stated in Food and Drug Administration, CFR, Title 21, Section 172,615, as "Masticatory Substances of Natural Vegetable Origin", or synthetic elastomers, such as styrene butadiene gum (SBR), butyl gum (isobutylene isoprene copolymer), or polyisobutylene (as stated in the above section of FDA under Masticatory Substances, Synthetic).

The inorganic fillers that form part of the chewing gum base includes calcium carbonate, talc, sodium sulphate, aluminium oxide, magnesium carbonate, kaolin, silicium oxide and calcium phosphates alone or in a mixture of more thereof. Waxes and fats are conventionally used for the adjustment of the consistency and softening of the chewing gum base when preparing chewing gum bases. In connection with the present invention any conventionally used and suitable type of wax may be used, such as for instance rice bran wax, polyethylene wax, petroleum wax (refined paraffin and micro crystalline wax), paraffin, beeswax, carnauba wax, candelilla wax, cocoa butter, degreased cocoa powder and any suitable oil or fat, as for instance completely or partially hydrogenated vegetable oils or completely or partially hydrogenated animal fats. In a preferred embodiment, the chewing gum is wax free. The wax of the general formulations may be replaced with hydrogenated oil or fat.

To soften the gum base further and to provide it with water binding properties, which gives the gum bases a pleasant smooth surface and reduces its adhesive properties, one or more emulsifiers may usually be added. Mono and diglycerides of edible fatty acids, lactic acid esters and acetic acid esters of mono and diglycerides of edible fatty acids, acetylated mono and diglycerides, sugar esters of edible fatty acids, Na-, K-, Mg- and Ca-stearates, lecithin, hydroxylated lecithin and the like may be mentioned as examples of legal and conventionally used emulsifiers added to the chewing gum base. In case of the presence of an active ingredient, the formulation may comprise certain specific emulsifiers and/or solubilizers in order to disperse and release the active ingredient.

Emulsifiers are conventionally used in quantities of 0–18 weight-%, preferably 0–12 weight-% of the gum base. Furthermore, the chewing gum base may optionally contain the usual additives, such as antioxidants, for instance BHT, BHA, propylgallate and tocopherols as well as preservatives and colorants.

Resins should also be mentioned as a component forming part of a chewing gum base, said resins being used to obtain the right chewing consistency and as plasticizer for the elastomers of the chewing gum base.

The chewing gum may also comprise the following surfactants and/or solubilizers, especially when active ingredients are present. As examples of types of surfactants to be used as solubilizers in a chewing gum composition according to the invention reference is made to H. P. Fiedler, Lexikon der Hilfstoffe für Pharmacie, Kosmetik und Angrenzende Gebiete, page 63–64 (1981) and the lists of approved food emulsifiers of the individual countries.

Anionic, cationic, as well as amphoteric, and nonionic solubilizers can be used, but usually the solubilizer used is either: anionic or nonionic as mainly such solubilizers are approved for use in food or medicines. In cases where the active agent is reactive it is usually an advantage to use a nonionic solubilizer as such are not very reactive and therefore do not affect the stability of the active agent unfavourably.

Suitable solubilizers include lecithines, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids, which solubilizers are all known for use as food emulsifiers, and polyoxyethylated hydrogenated castor oil (for instance such sold under the trade name CREMOPHOR), blockcopolymers of ethylene oxide and propylene oxide (for instance as sold under the trade name PLURONIC or the trade name POLOXAMER), polyoxyethylene fatty alcohol ethers, polyoxyethylene sorbitan fatty acid esters, sorbitan esters of fatty acids and polyoxyethylene steraric acid ester, all known in the EEC for use as pharmaceutical-cosmetical emulsifiers.

Particularly suitable solubilizers are polyoxyethylene stearates, such as for instance polyoxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllatylate, sodium laurylsulfate, polyoxyethylated hydrogenated castor oil, blockcopolymers of ethylene oxide and propyleneoxide and polyoxyethylene fatty alcohol ether. The solubilizer may either be a single compound or a combination of several compounds. The expression "solubilizer" is used in the present text to describe both possibilities, the solubilizer used must be suitable for use in food and/or medicine.

In the presence of an active ingredient the chewing gum may preferably also comprise a carrier known in the art.

In a further embodiment according to the invention the chewing gum also comprise a fatty acid sucrose ester such as palmitatetstearate sucrose ester. The palmitate/stearate sucrose ester may enhance the flavour release and/or increase release of an active ingredient. Preferably, the content of palmitate of the sucrose ester is above 50% of the weight of fatty acids of the sucrose ester.

Examples of active agents in the form of compounds for the care of treatment of the oral cavity and the teeth, are for instance bound hydrogen peroxide and compounds capable of releasing urea during chewing.

Examples of active agents in the form of antiseptics are for instance salts and compounds of guanidine and biguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophens, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. Furthermore Martindale, The Extra Pharmacopoeia, 28th edition, page 547–578; metal salts, complexes and compounds with limited water-solubility, such as aluminium salts, (for instance aluminium potassium sulfate AIK(SO4)2, 12H2O) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodiummonofluorophosphate, aminofluorides, stannous fluoride), phosphates, carbonates and selenium.

Confer furthermore J. Dent.Res. Vol. 28 No. 2, page 160–171, 1949, wherein a wide range of tested compounds are mentioned.

Examples of active agents in the form of agents adjusting the pH in the oral cavity include for instance: acceptable acids, such as adipinic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

Other active ingredients include beta-lupeol, Letigen®, Sildenafil citrate and derivatives thereof.

In one embodiment where the preparation according to the invention comprises an active ingredient, up to 50 weight-%, preferably 0.1–10 weight-% active agent may be in the form of a solid dispersion hereof in a carrier, up to 60 weight-%, preferably approximately 20 weight-% of the carrier used to obtain the solid dispersion, 0.1–30 weight-%, preferably 0.1–10 weight-% solubilizer, 15–80 weight-%, preferably approximately 35 weight-% chewing gum base and up to 85 weight-%, preferably approximately 35 weight-% auxiliary substances and additives.

The invention further relates to a process for the preparation of a chewing gum composition, which process is characterised by preparing a chewing gum base on the basis of conventional chewing gum base constituents.

The formulation of the chewing gum base depends on the type of chewing gum desired as described above or the required type of structure. Suitable raw materials for the gum base comprise substances according to U.S. Chewing Gum Base Regulations—Code of Federal Regulations, Title 21, Section 172.615.

It is a particular advantage of the invention that the chewing gum composition can be prepared using conventional ingredients, conventional equipment and conventional methods of preparation.

The chewing gum product may be of any known type, such as bubble gum, bits, optionally provided with a dragee, and sticks or chewing gum of any other desired form. The chewing gum pieces may be coated with a type of wax, a film coating or a conventional so-called candy coat based on sugar-containing or sugar free substances.

A single piece of chewing gum usually weighs between 0.4 and 20.0 g. The following Table indicates the preferred intervals for the different product types:

| | |
|---|---|
| Chewing gum bits | 500–3,500 mg |
| Coated chewing gum | 600–6,000 mg |
| Chewing gum sticks | 1,000–5,000 mg |

When the individual ingredients forming part of a chewing gum composition according to the invention are mentioned in singular, such mention also comprises a combination of several such ingredients, apart from instances where one particular ingredient is mentioned.

PREPARATION OF CHEWING GUM

Figure 1:
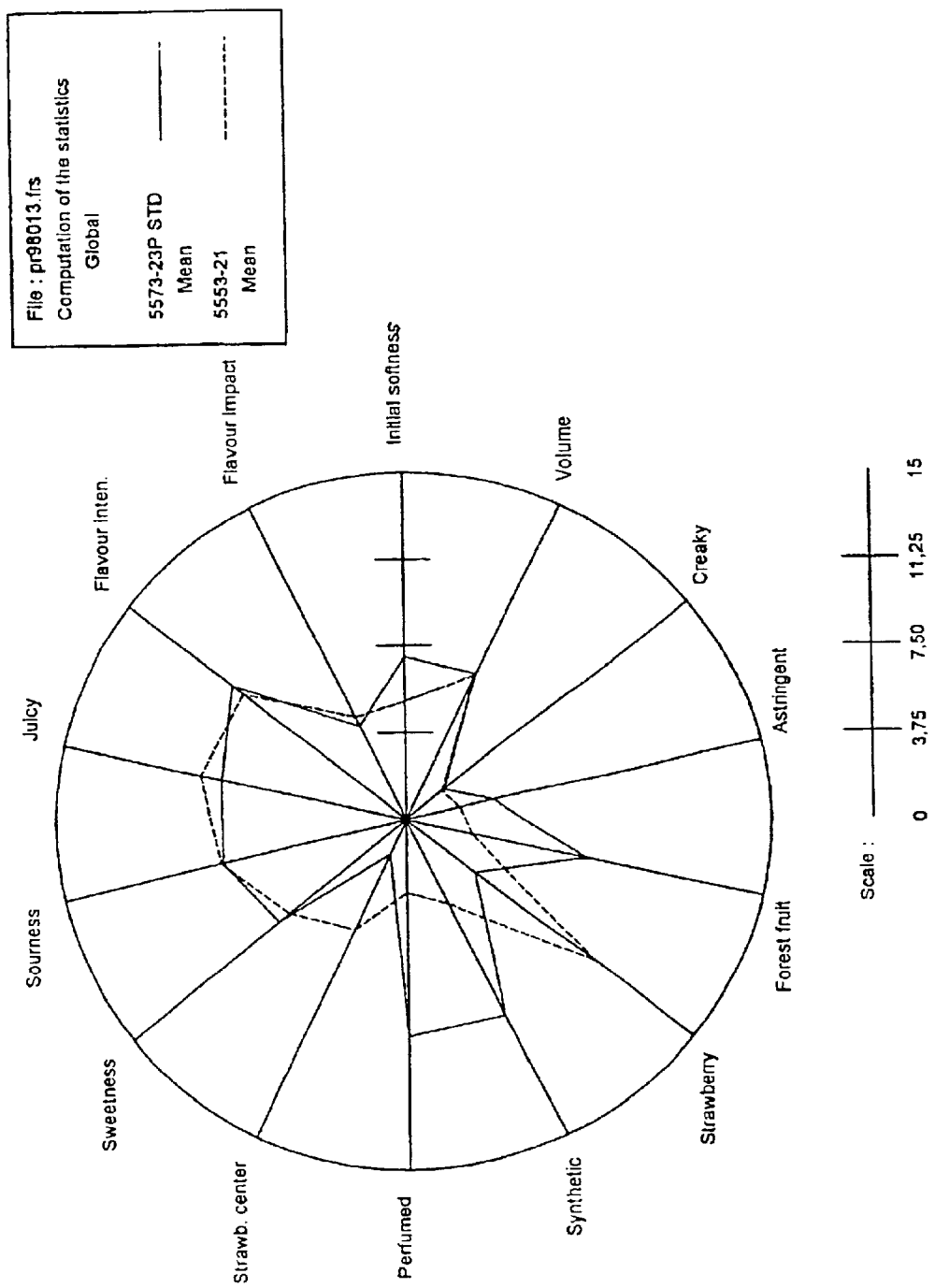
FIG. 1. shows the initial phase of test profile 1.
Figure 2:
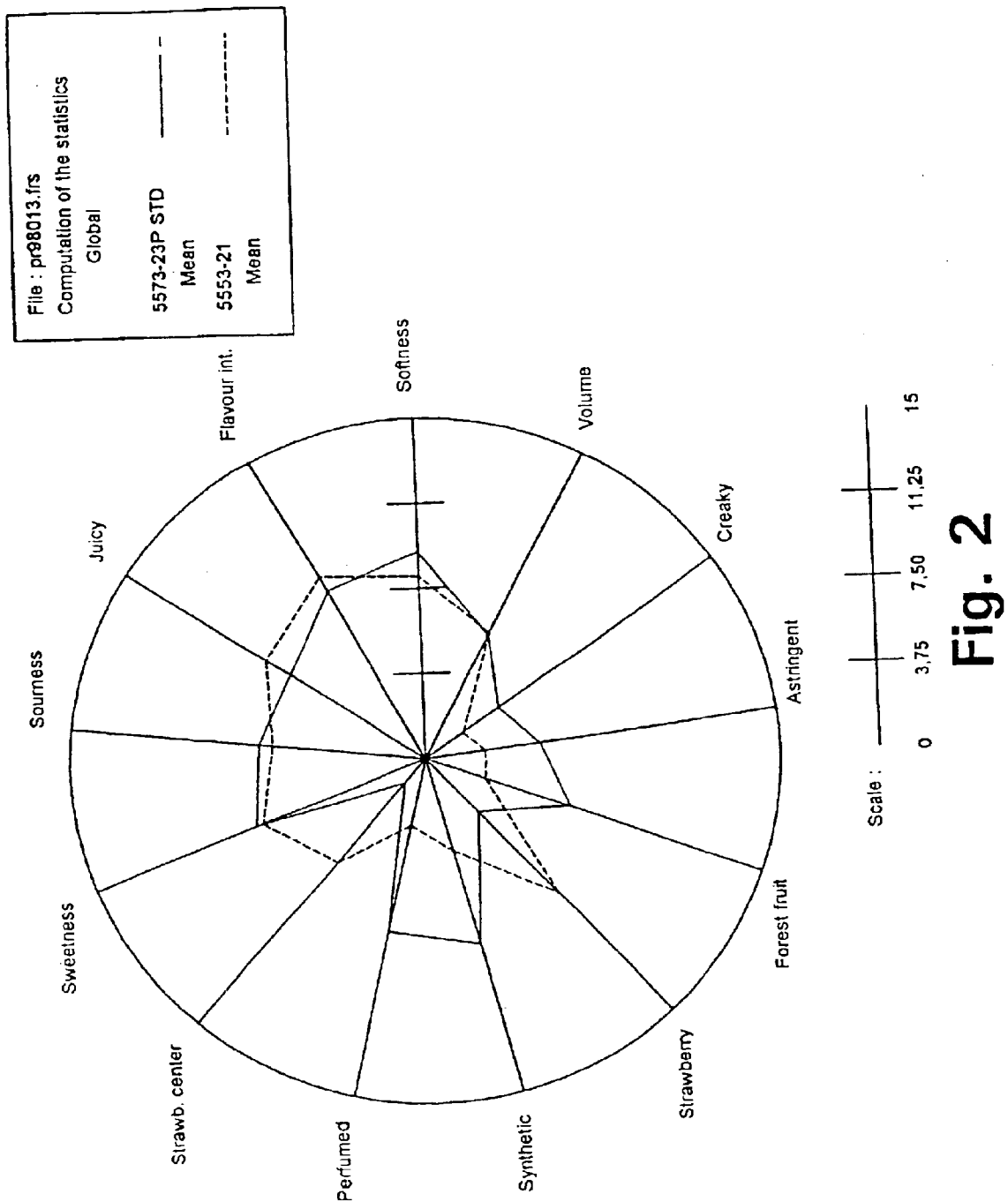
FIG. 2. shows the intermediate phase I of test profile 1.
Figure 3:
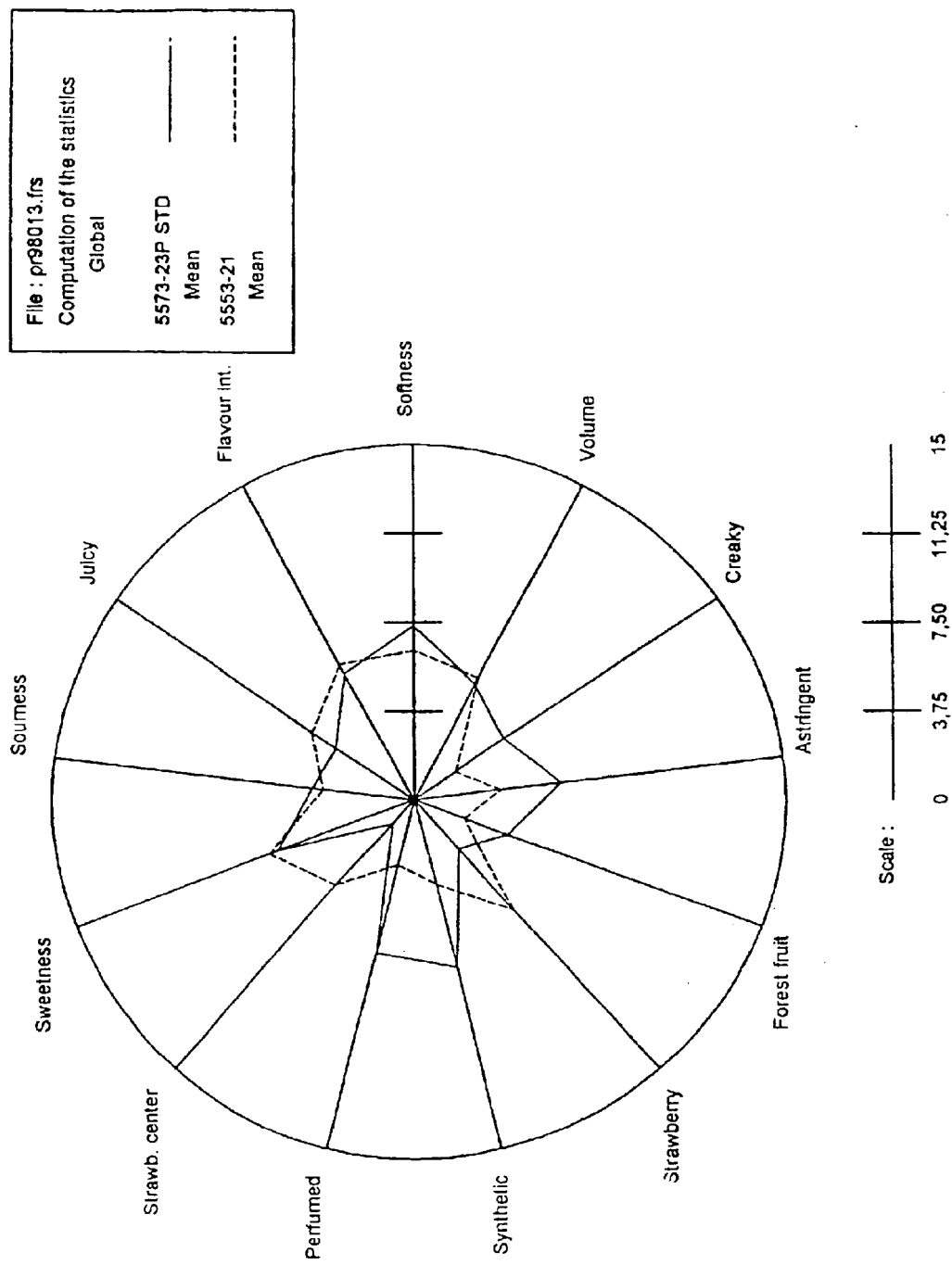
FIG. 3. shows the intermediate phase II of test profile 1.
Figure 4:
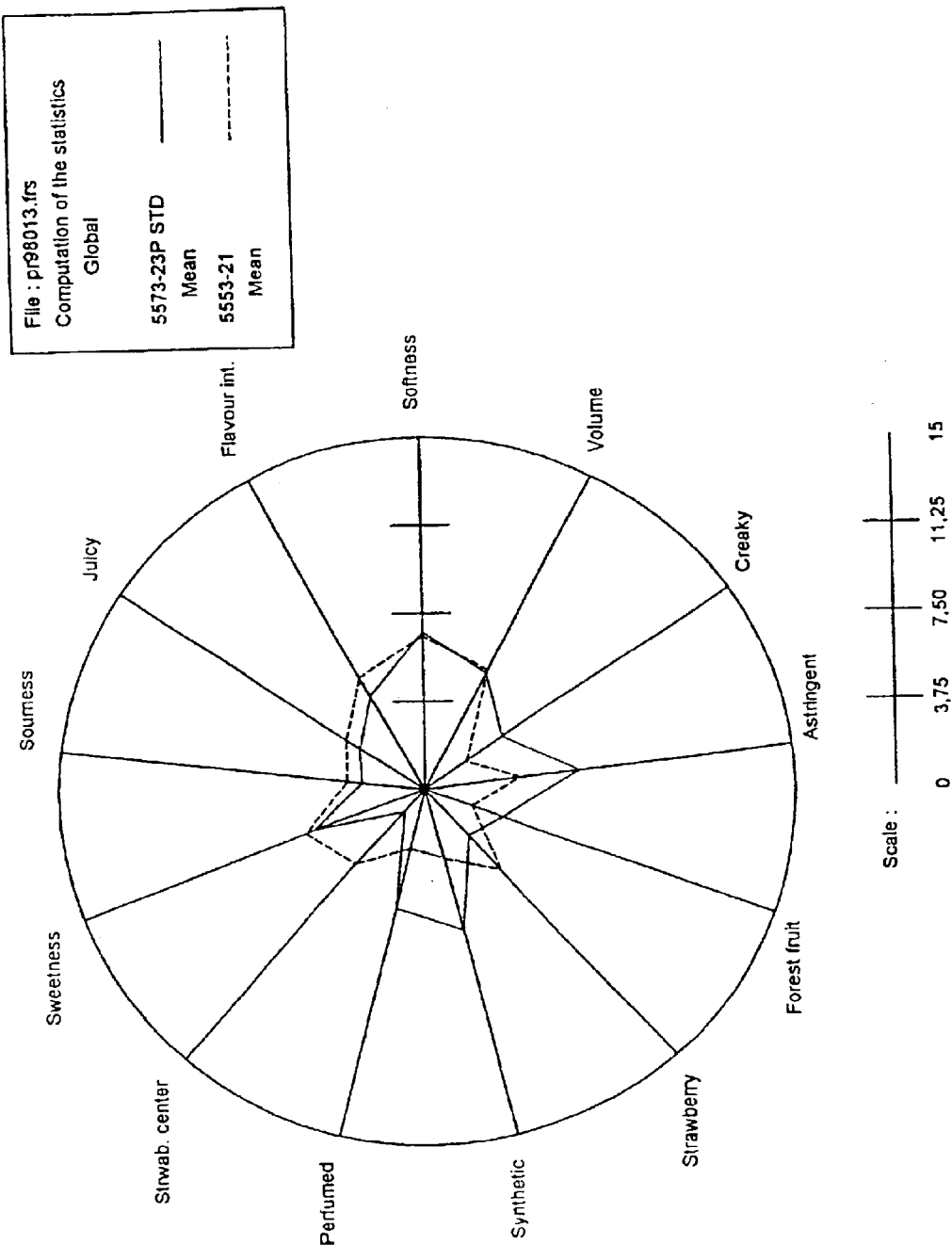
FIG. 4. shows the end phase of test profile 1.
Figure 5:
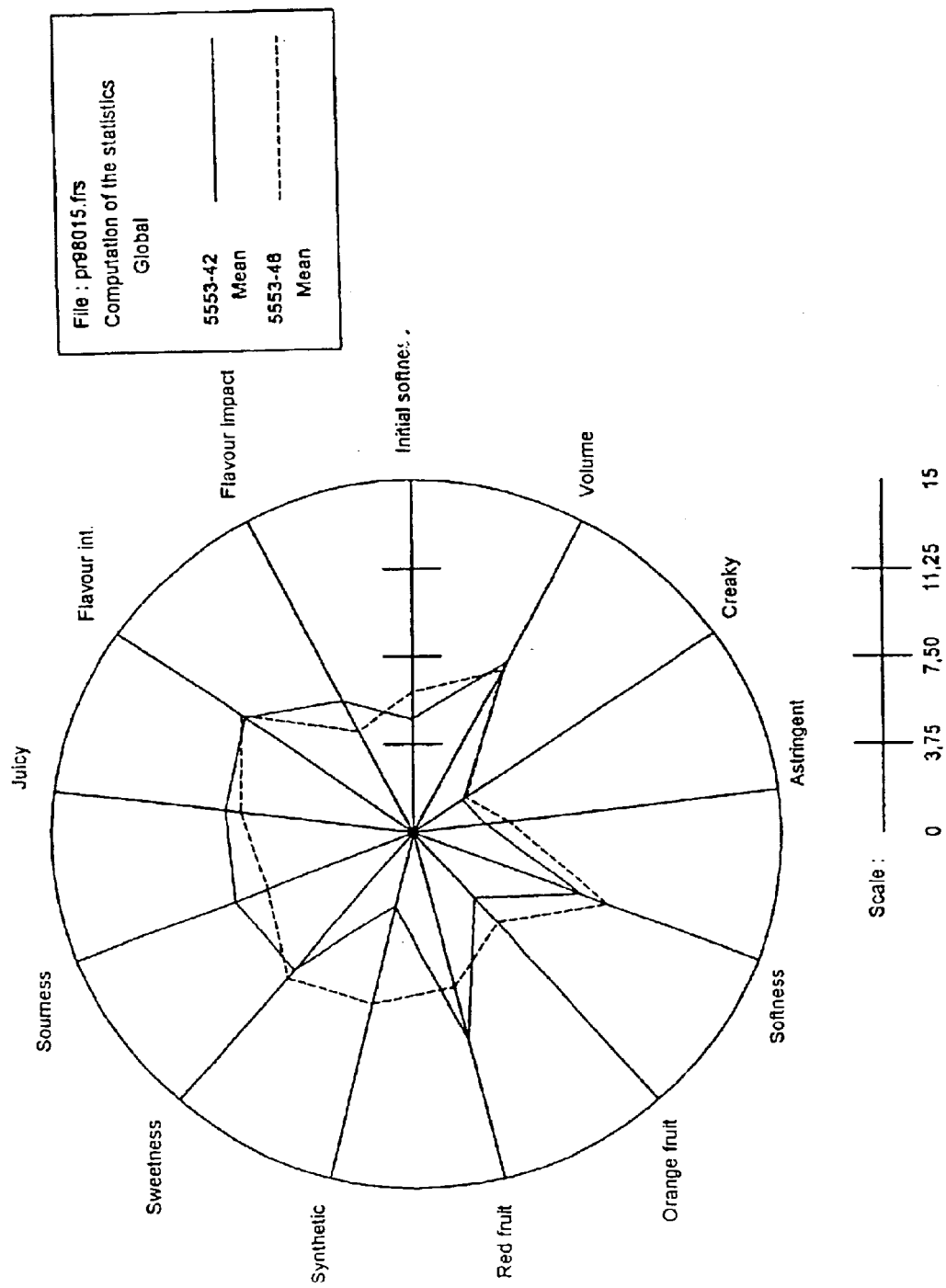
FIG. 5. shows the initial phase of test profile 2.
Figure 6:
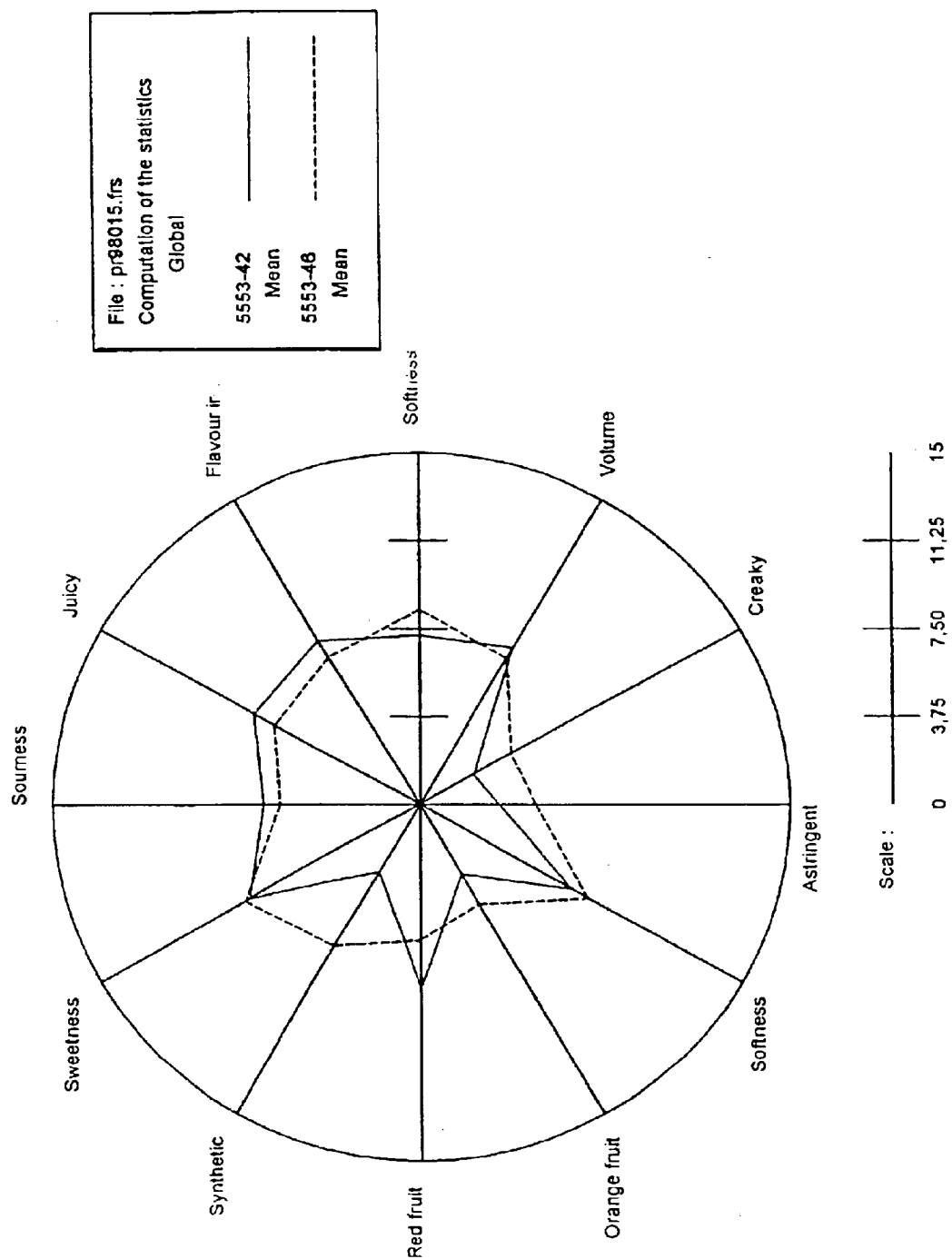
FIG. 6. shows the intermediate phase I test profile 2.
Figure 7:
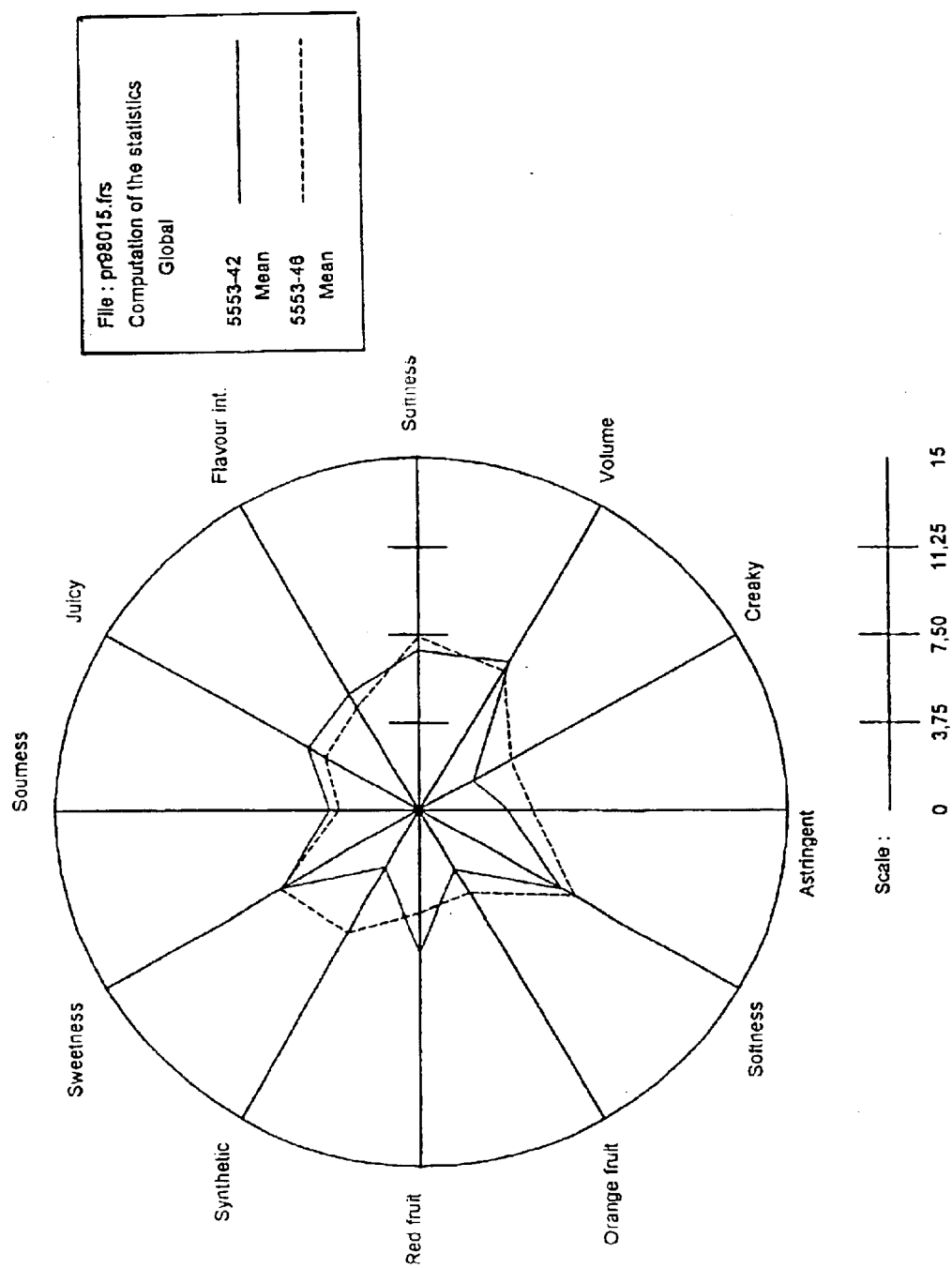
FIG. 7. shows the intermediate phase II of test profile 2.
Figure 8:
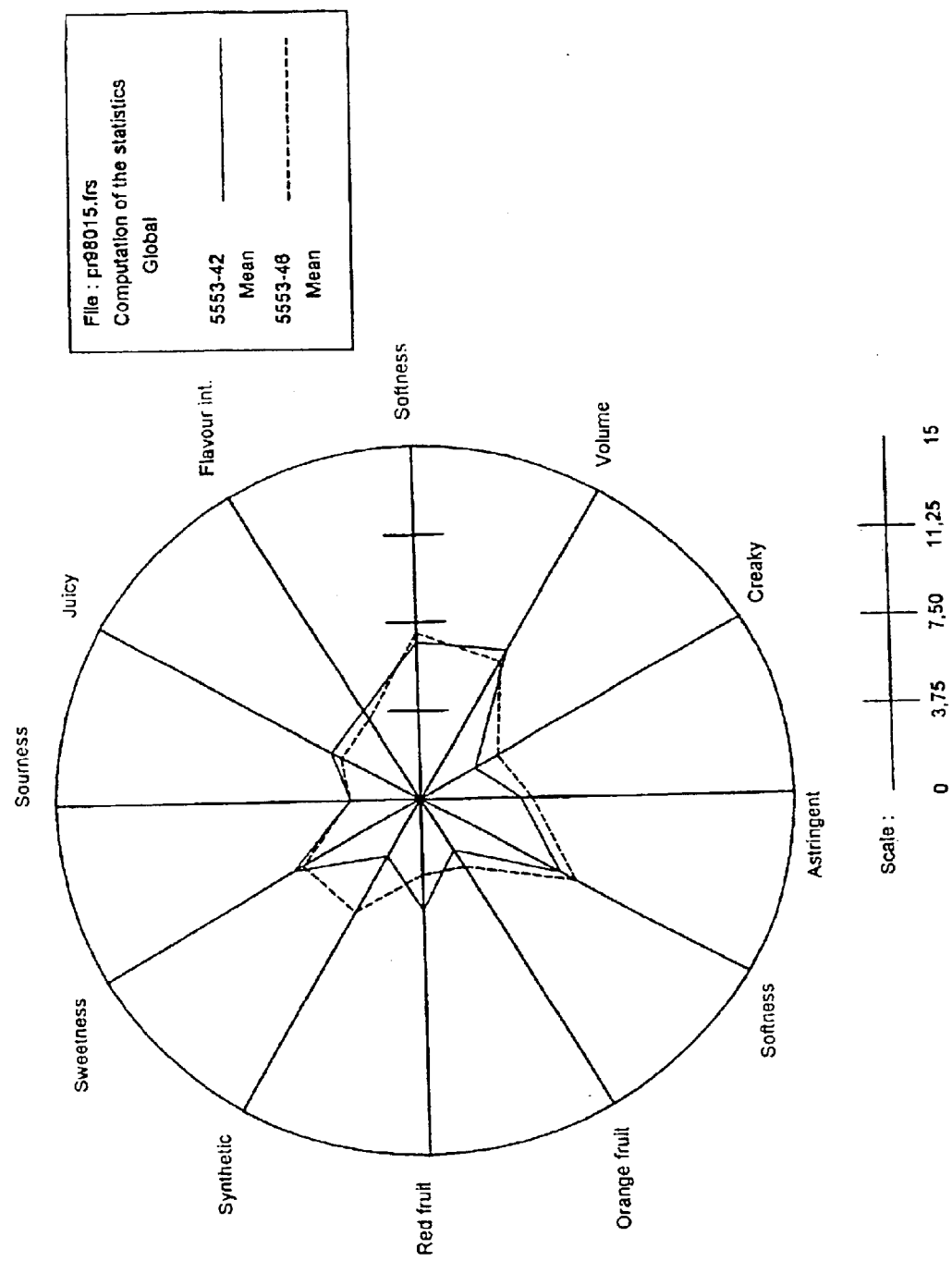
FIG. 8. shows the end phase of test profile 2.
Figure 9:
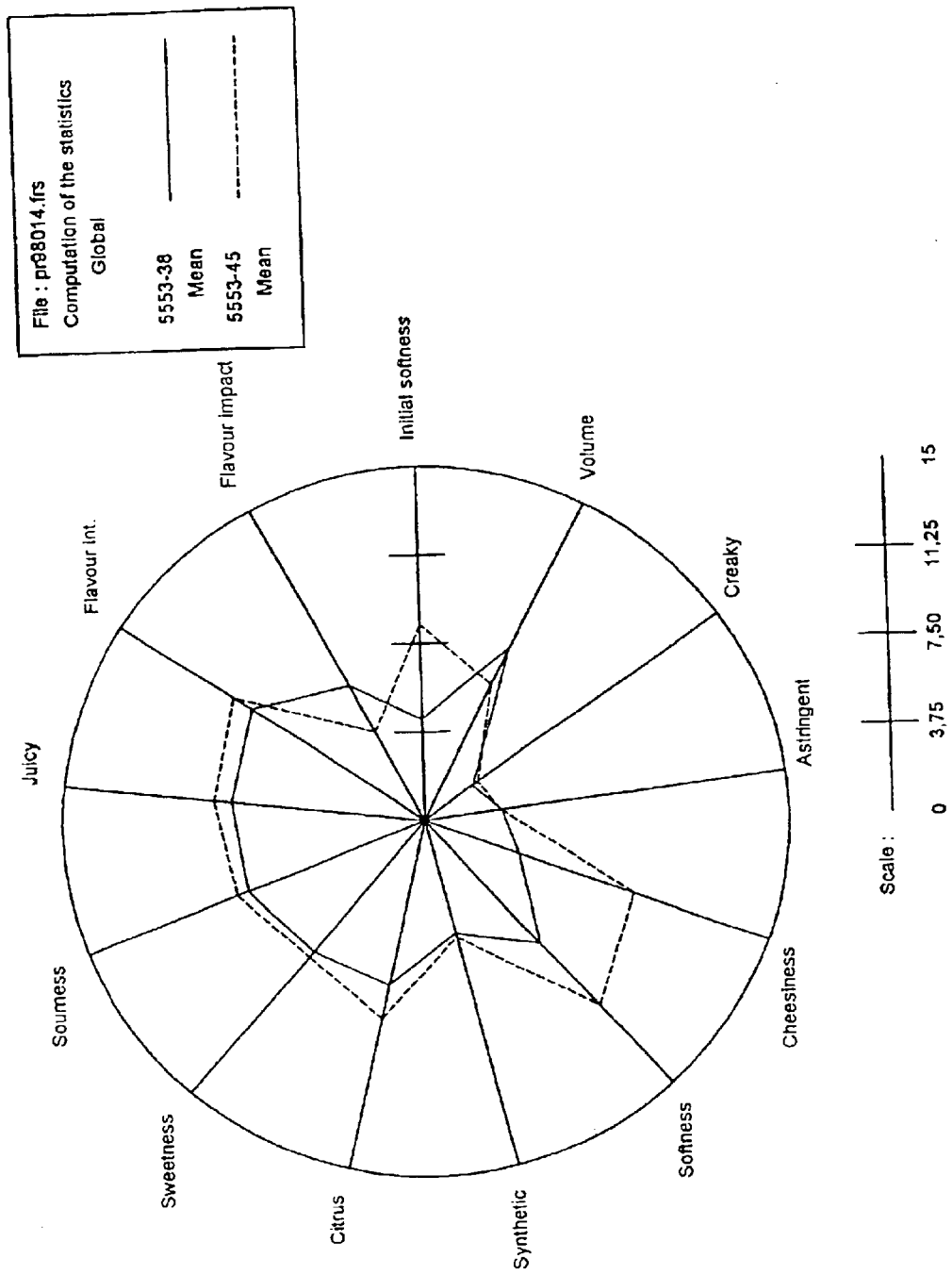
FIG. 9. shows the initial phase of test profile 3.
Figure 10:
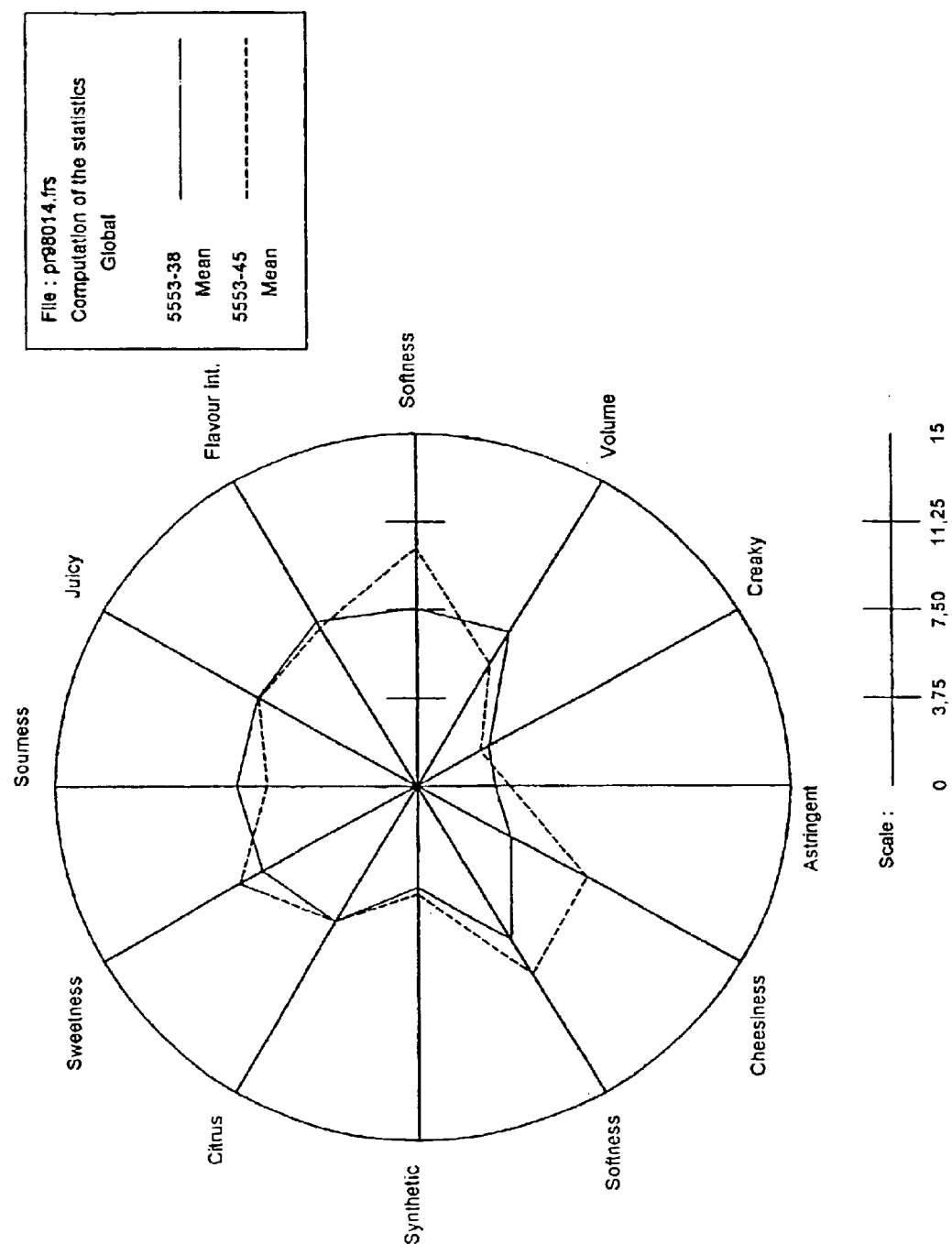
FIG. 10. shows the intermediate phase I of test profile 3.
Figure 11:
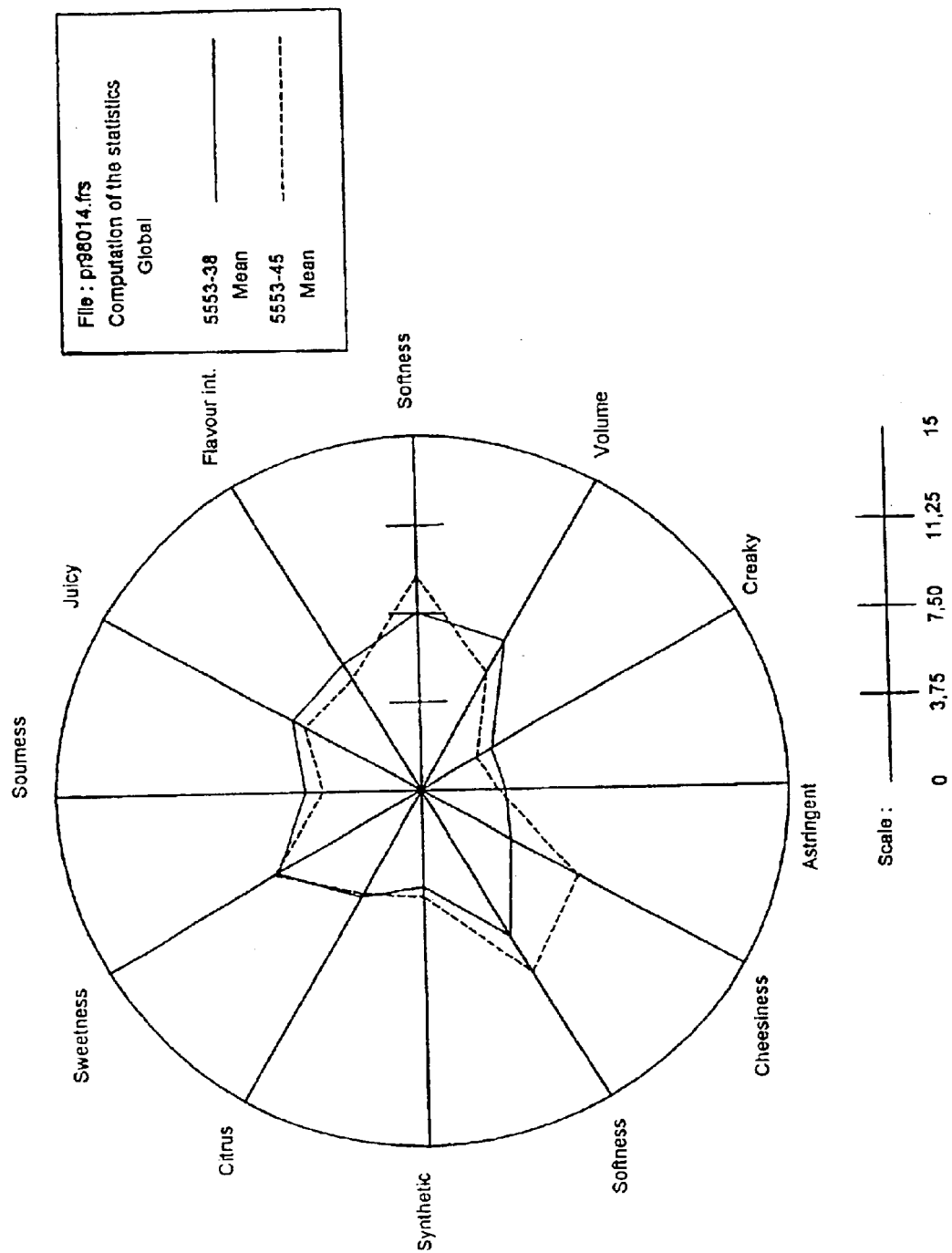
FIG. 11. shows the intermediate phase II of test profile 3.
Figure 12:
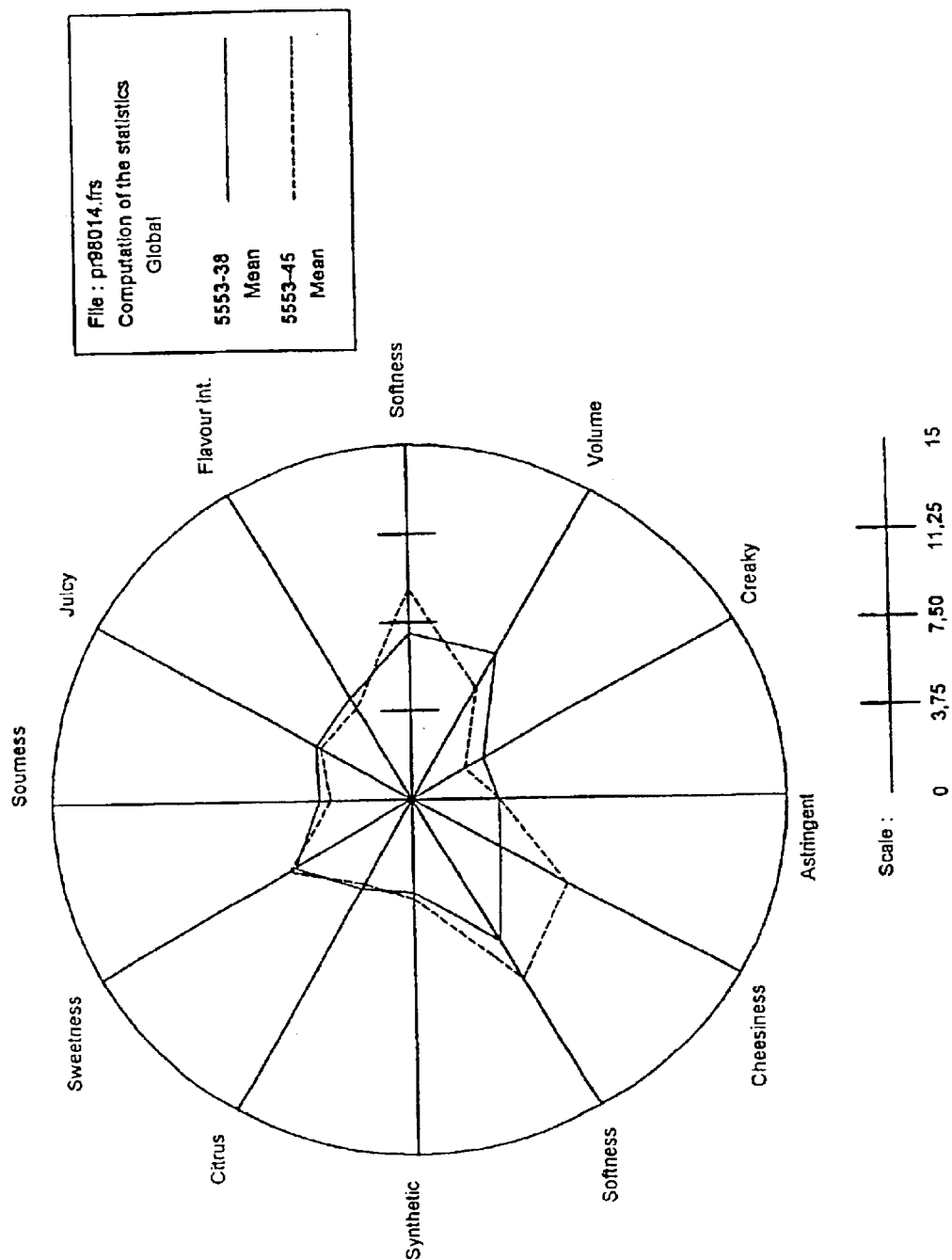
FIG. 12. shows the end phase of test profile 3.

The preparation process comprises the following:

Mixing of conventional chewing gum components in kneading kettles (mixers) with strong horizontally placed Z-shaped arms, which processes the raw materials and produces a homogeneous gum mass.

The kneading kettles are heated to a temperature of 30–80° C., typically approx. 45° C. The mixing process starts with gum base quantities that have been weighed out, and the processing of these lasts for 1–20 minutes, typically approx. 10 minutes. Then one or more sweeteners) in powder form or in liquid form is/are added. The dosage of sweeteners and the following processing last from 1 to 20 minutes, typically approx. 7 minutes.

Then the flavours and the remaining components are added and kneaded for a further 1 to 10 minutes, typically approx. 5 minutes. The admixture of flavours and the remaining components may also take place in the beginning of the kneading process, i.e. before the admixture of the sweeteners. It is also possible to add flavours in two or more portions during the kneading process.

When the kneading is completed, the kneading kettle is tipped, and the gum mass is taken out into carts, onto trays or the like.

The next process is the forming of the chewing gum. Before the forming can take place, the chewing gum mass, however, must be cooled. When taken out, the chewing gum mass has a temperature of 50–70° C., and in order to form the chewing gum, the temperature must be reduced to 30–45° C. The cooling of the chewing gum either takes place by storing the chewing gum mass in carts or on trays for quite a long time or by transporting a thin chewing gum carpet through a cooling tunnel.

The forming of the chewing gum may take place by extrusion through a specially formed nozzle, or the chewing gum may be formed after extrusion by means of rollers, punching machines, tenterng wheels, and the like.

The chewing gum may be formed into cores, sticks, balls, cubes, cylinders, and many other shapes.

In order to prevent the chewing gum from sticking to the rollers and other tools, the chewing gum is frequently powdered with a powder, which may consist of i.e. icing sugar, talc, corn flour, and the like.

The formed chewing gum can be cooled immediately to room temperature in a cooling tunnel and be packed (especially in case of bubble gum and soft bubble gum), or the cooling may take place on trays at the store for semi-manufactured products at a controlled temperature and moisture.

The formed and cooled chewing gum is then treated by means coating and polishing processes before the packing.

Coating and Polishing of Cores of Chewing Gum

The coating of cores takes place in tilted, round or horizontally placed cylindrical coating kettles that rotate during the whole process. The coating kettles are made from copper, stainless steel or fiberglass-reinforced polyester, and are often equipped with a piping system that supplies and exhausts air and doses the coating suspension.

The coating process may take place as follows:

Cores of chewing put into movement in rotating coating kettles are added to the coating suspension in small portions that disperse evenly over the surfaces of the cores after a short or long smoothing out time. (The smoothing out time is the period of time during which the suspension disperses over the cores, approx. 10–90 seconds, preferably approx. 30–60 seconds). Afterwards the cores are dried by means of air. The operation is repeated up to 90 times, preferably approx. 30–40 times, until the cores are completely covered and have the preferred measure and the preferred weight.

In order to ease the coating process of chewing gum, a suspension is used which is heated up to 90° C., preferable up to about 75° C., and air which is heated up to at least 35° C. such as about 40° C.

Between the dosages of the coating suspension, one or more active substance(s) in solid form is/are added in one or more increment(s) in order to provide the chewing gum with a fast effect, e.g. flavour release during the chewing. It is an important aspect of the invention that the drying period is extended to after applying the active substances. When the active substances are added just after the coating process is completed, the coating suspension is still soft and the active substances may be more or less embedded in the coating in the solid form. The skilled person will be able to estimate or to establish by a simple test when the active substance should be added for obtaining a sufficient adherence of the active ingredient to the coating.

As appears from the Examples, the drying period is 0 seconds, however, drying periods up to 50 seconds such as up to 25 seconds are within the present invention and even longer periods may be acceptable depending on the drying properties of the coating suspension, the particle size of the active substance as well as whether it is desired that the active substance should be fully embedded in the coating or should form a superficial layer on the coating.

Furthermore, between the dosages of the coating suspension and the addition of one or more active substance(s) in solid form, one or more active substances in liquid all form may be added.

In order to achieve a neat and smooth surface of the chewing gum tablets with the completed coating, these may subsequently be subjected to a polishing. The polishing also takes place in rotating coating kettles in which a polishing suspension or a polishing powder is added to the coated cores in one or more portion(s). The polishing suspension often consists of wax, emulsifier, shellac, gum arabic, water, etc. The polishing powder often consists of wax only, or of wax mixed with emulsifier, gum arabic or talc, etc.

The present invention is further illustrated below by means of some examples.

EXAMPLES

As a starting point, partly sugar-containing, partly sugar-free cores of chewing gum are used which are rolled out into sheets by means of stamping rollers, i.e. coherent sheets of cores of chewing gum which have a weight of approx. 0.9 g/piece.

A coating kettle DRIA 1200, supplied by Driam Metallprodukt GmbH, Germany, is used for the coating of the above-mentioned cores. DRIA 1200 is a horizontally placed and cylindrical kettle intended for the coating of 50 kg of chewing gum cores. The equipment has computer controlling of the amount of dosages of liquid and solid substances as well as controlling of the smoothing out times, the drying times, air quantities, the temperature of the drying air, and the airflow direction. For dosage of an active substance in a solid form, a pneumatic conveyor having a dispersing arm which ensures an even dispersion of the powder over all the tablets. The coating kettle can be set at various velocities from 1 to 15 rpm.

During the coating process, 50 kg of chewing gum cores are filled into the coating kettle that can be set to a rotation of 8 rpm. During this rotation, the cores of chewing gum are separated from each other. Drying air is applied to the equipment, and surplus talc, which has been added during the rolling out of the cores of chewing gum, is removed. This separation and blowing through of air last for approx. 5 minutes.

Then the rotation speed of the coating kettle is increased to 11 rpm, and the first dosage of the coating suspension may take place.

It is also possible to use small (2 kg) or large (100 kg) tilted, round coating kettles and sprinkle active substance in solid form manually in 1–10 increment(s) between the dosages of the coating suspension. Dosage of active substance in more increments ensures an even dispersion of the powder over all the cores of chewing gum.

For the coating of sugar-containing cores of chewing gum, a saccharose suspension was used in the following examples, and a sorbitol suspension was used for the coating of sugar-free cores.

In the following embodiments, the coating suspension had the following composition:

| | |
|---|---:|
| 1. Saccharose suspension | |
| Sugar juice (70%) | 94.45% |
| Water | 4.68% |
| Gelatine (Bloom value 120–160) | 0.87% |
| Total | 100.00% |
| 2. Sorbitol suspension | |
| Sorbitol liquid/neosorb 70/02 | 97.86% |
| Water | 1.59% |
| Titanium dioxide | 0.55% |
| Total | 100.00% |

Example 1

Coating in DRIA 1200 equipment of 50 kg of sugar-containing chewing gum cores with peppermint taste.

| Saccharose suspension Dosage No. | Amount of dosage G | Smoothing out time sec. | Drying time sec. | Drum rpm |
|---|---|---|---|---|
| 1–2 | 500 | 45 | 300 | 11 |
| 3–12 | 900 | 45 | 400 | 11 |
| 13 | 600 + 222* | 60 | 400 | 11 |
| 14–15 | 700 | 0 | 380 | 11 |
| 16–21 | 1000 | 0 | 380 | 11 |
| 22–34 | 1000 | 30 | 410 | 11 |
| 35–38 | 600 | 260 | 280 | 11 |
| 39 | 500 | 1500 | 290 | 11 |
| 40 | wax powder 50 g | 300 | 300 | 8 |

*A 600 g saccharose suspension + 222 g peppermint oil.

Example 2

5573-23 (Standard)

Coating in DRIA 1200 equipment of 50 kg of sugar-free chewing gum cores with strawberry taste.

| Sorbitol suspension Dosage No. | Amount of dosage G | Smoothing out time sec. | Drying time sec. | Drum rpm |
|---|---|---|---|---|
| 1–2 | 400 | 0 | 250 | 11 |
| 3–5 | 700 | 15 | 300 | 11 |
| 6 | 700 + 275* | 60 | 300 | 11 |
| 7–16 | 700 | 45 | 300 | 11 |
| 17–24 | 1000 | 45 | 350 | 11 |
| 25–26 | 700 | 240 | 240 | 11 |
| 27 | wax powder 50 g | 360 | 360 | 8 |

*A 700 g sorbitol suspension + 275 g strawberry flavour.

Example 3

5553-21

Coating in DRIA 1200 equipment of 50 kg sugar-free chewing gum cores with strawberry taste.

| Sorbitol suspension Dosage No. | Amount of dosage G | Smoothing out time sec. | Drying time sec. | Drum rpm |
|---|---|---|---|---|
| 1–2 | 400 | 0 | 250 | 11 |
| 3–5 | 700 | 15 | 300 | 11 |
| 6 | 350 | 10 | 0 | 11 |
| 7 | 250* powder | 60 | 0 | 11 |
| 8–9 | 700 | 10 | 300 | 11 |
| 10 | 350 | 10 | 0 | 11 |
| 11 | 250* powder | 60 | 0 | 11 |
| 12–13 | 700 | 10 | 300 | 11 |
| 14–18 | 700 | 45 | 300 | 11 |
| 19–26 | 1000 | 45 | 350 | 11 |
| 27–28 | 700 | 240 | 240 | 11 |
| 29 | wax powder 50 g | 360 | 360 | 8 |

*The freeze-dried strawberry powder.

Example 4

5553-46 (Standard)

Coating in tilted kettles of 2 kg sugar-free chewing gum cores with a forest fruit taste.

| Sorbitol suspension Dosage No. | Amount of dosage G | Smoothing out time sec. | Drying time sec. | Number of revolutions rpm |
|---|---|---|---|---|
| 1 | 20 | 120 | 120 | 50 |
| 2 | 20 | 90 | 120 | 50 |
| 3 | 20 | 60 | 60 | 50 |
| 4–9 | 30 | 30 | 90 | 50 |
| 10–11 | 30 | 30 | 120 | 50 |
| 12 | 20* | 60 | 120 | 50 |
| 13 | 5 raspberry flavour | 10 | 0 | 50 |
| 14 | 20 | 40 | 0 | 50 |
| 15–16 | 20 | 5 | 120 | 50 |
| 17–22 | 30 | 60 | 120 | 50 |
| 23–26 | 40 | 30 | 120 | 50 |
| 27–33 | 30 | 60 | 120 | 50 |
| 34–35 | 20 | 120 | 240 | 50 |
| 36 | Wax powder 2 g | 300 | 300 | 50 |

*A sorbitol suspension with 7.5% aspartame.

Example 5

5553-42

Coating in tilted round kettles of 2 kg sugar-free chewing gum cores with forest fruit taste.

| Sorbitol suspension Dosage No. | Amount of dosage G | Smoothing out time sec. | Drying time sec. | Number of revolutions rpm |
|---|---|---|---|---|
| 1 | 20 | 120 | 120 | 50 |
| 2 | 20 | 90 | 120 | 50 |
| 3 | 20 | 60 | 60 | 50 |
| 4–9 | 30 | 30 | 90 | 50 |
| 10–11 | 30 | 30 | 120 | 50 |
| 12 | 20* | 60 | 120 | 50 |
| 13 | 20 | 10 | 0 | 50 |
| 14 | 20** powder | 40 | 0 | 50 |
| 15–16 | 20 | 5 | 120 | 50 |
| 17–19 | 30 | 60 | 120 | 50 |
| 20–28 | 40 | 30 | 120 | 50 |
| 29–33 | 30 | 60 | 120 | 50 |
| 34–35 | 20 | 120 | 240 | 50 |
| 36 | Wax powder 2 g | 300 | 300 | 50 |

*A sorbitol suspension with 7.5% aspartame.
**A freeze-dried raspberry powder.

Example 6

5553-45 Standard

Coating in tilted kettles of 2 kg sugar-free chewing gum cores with orange, lemon, and pink grape flavour.

| Sorbitol suspension Dosage No. | Amount of dosage G | Smoothing out time sec. | Drying time sec. | Number of revolutions rpm |
|---|---|---|---|---|
| 1 | 20 | 120 | 120 | 50 |
| 2 | 20 | 90 | 120 | 50 |
| 3 | 20 | 60 | 60 | 50 |
| 4–9 | 30 | 30 | 90 | 50 |
| 10–11 | 30 | 30 | 120 | 50 |
| 12 | 20* | 60 | 120 | 50 |
| 13 | 6.5** flavour | 10 | 0 | 50 |
| 14 | 20 | 40 | 0 | 50 |
| 15–16 | 20 | 5 | 120 | 50 |
| 17–18 | 30 | 60 | 120 | 50 |
| 19 | 30 | 60 | 120 | 50 |
| 20 | 30 | 60 | 120 | 50 |
| 21–22 | 30 | 60 | 120 | 50 |
| 23–24 | 40 | 30 | 120 | 50 |
| 25–28 | 40 | 30 | 120 | 50 |
| 29–35 | 30 | 60 | 120 | 50 |
| 36–37 | 20 | 120 | 240 | 50 |
| 38 | wax powder 2 g | 300 | 300 | 50 |

*A sorbitol suspension with 7.5% aspartame.
** 5 g orange flavour, 1 g lemon flavour and 0.5 g pink grape flavour.

Example 7

5553-38

Coating in tilted kettles of 2 kg sugar-free chewing gum cores with a mixture of orange and pink grape flavour, and freeze-dried orange and lemon powder.

| Sorbitol suspension Dosage No. | Amount of dosage G | Smoothing out time sec. | Drying time sec. | Number of revolutions rpm |
|---|---|---|---|---|
| 1 | 20 | 120 | 120 | 50 |
| 2 | 20 | 90 | 120 | 50 |
| 3 | 20 | 60 | 60 | 50 |
| 4–9 | 30 | 30 | 90 | 50 |
| 10–11 | 30 | 30 | 120 | 50 |
| 12 | 20* | 60 | 120 | 50 |
| 13 | 3.5** flavour | 10 | 0 | 50 |
| 14 | 20 | 40 | 0 | 50 |
| 15–16 | 20 | 5 | 120 | 50 |
| 17–18 | 30 | 60 | 120 | 50 |
| 19 | 20 | 10 | 0 | 50 |
| 20 | 15*** powder | 40 | 0 | 50 |
| 21–22 | 20 | 5 | 120 | 50 |
| 23–24 | 30 | 60 | 120 | 50 |
| 25–28 | 40 | 30 | 120 | 50 |
| 29–35 | 30 | 60 | 120 | 50 |
| 36–37 | 20 | 120 | 240 | 50 |
| 38 | wax powder 2 g | 300 | 300 | 50 |

*A sorbitol suspension with 7.5% aspartame.
**2 g orange flavour, 1 g lemon flavour, and 0.5 g pink grape flavour.
***A freeze-dried orange powder.

Example 8

Coating in tilted kettles of 2 kg sugar-free chewing gum cores with a mixture of peppermintoil, menthol, and freeze-dried powder of peppermint leaves and stems (Mentha piperita).

| Sorbitol suspension Dosage No. | Amount of dosage G | Smoothing out time sec. | Drying time sec. | Number of revolutions rpm |
|---|---|---|---|---|
| 1 | 20 | 120 | 120 | 50 |
| 2 | 20 | 90 | 120 | 50 |
| 3 | 20 | 60 | 60 | 50 |
| 4–9 | 30 | 30 | 90 | 50 |
| 10–11 | 30 | 30 | 120 | 50 |
| 12 | 20* | 60 | 120 | 50 |
| 13 | 7** mintoil | 10 | 0 | 50 |
| 14 | 20 | 40 | 0 | 50 |
| 15–16 | 20 | 5 | 120 | 50 |
| 17–18 | 30 | 60 | 120 | 50 |
| 19 | 20 | 10 | 0 | 50 |
| 20 | 10*** powder | 40 | 0 | 50 |
| 21–22 | 20 | 5 | 120 | 50 |
| 23–24 | 30 | 60 | 120 | 50 |
| 25–28 | 40 | 30 | 120 | 50 |
| 29–35 | 30 | 60 | 120 | 50 |
| 36–37 | 20 | 120 | 240 | 50 |
| 39 | wax powder 2 g | 300 | 300 | 50 |

*A sorbitol suspension with 2.5% aspartame.
**6 g peppermintoil and 1 g menthol.
***A powder of freeze-dried leaves and stems of peppermint.

Example 9

Coating in tilted kettles of 2 kg sugar-free chewing gum cores with spearmint oil and a powder of freeze-dried leaves and stems of spearmint (Mentha spicata).

| Sorbitol suspension Dosage No. | Amount of dosage g | Smoothing out time sec. | Drying time sec. | Number of revolutions rpm |
|---|---|---|---|---|
| 1 | 20 | 120 | 120 | 50 |
| 2 | 20 | 90 | 120 | 50 |
| 3 | 20 | 60 | 60 | 50 |
| 4–9 | 30 | 30 | 90 | 50 |
| 10–11 | 30 | 30 | 120 | 50 |
| 12 | 20* | 60 | 120 | 50 |
| 13 | 5.5** sp. oil | 10 | 0 | 50 |
| 14 | 20 | 40 | 0 | 50 |
| 15–16 | 20 | 5 | 120 | 50 |
| 17–19 | 30 | 60 | 120 | 50 |
| 19 | 20 | 10 | 0 | 50 |
| 20 | 10*** powder | 40 | 0 | 50 |
| 21–22 | 20 | 5 | 120 | 50 |
| 23–24 | 30 | 60 | 120 | 50 |
| 25–28 | 40 | 30 | 120 | 50 |
| 29–35 | 30 | 60 | 120 | 50 |
| 36–37 | 20 | 120 | 240 | 50 |
| 38 | Wax powder 2 g | 300 | 300 | 50 |

*A sorbitol suspension with 2.5% aspartame.
**5.5 g spearmintoil.
***10 g freeze-dried powder of leaves and stems of spearmint.

Example 10

Coating in tilted kettles of 2 kg sugar-free chewing gum cores with a mixture of liquid eucalyptus, menthol, anethol, and a powder of freeze-dried leaves of eucalyptus.

| Sorbitol suspension Dosage No. | Amount of dosage g | Smoothing out time sec. | Drying time sec. | Number of revolutions rpm |
| --- | --- | --- | --- | --- |
| 1 | 20 | 120 | 120 | 50 |
| 2 | 20 | 90 | 120 | 50 |
| 3 | 20 | 60 | 60 | 50 |
| 4–9 | 30 | 30 | 90 | 50 |
| 10–11 | 30 | 30 | 120 | 50 |
| 12 | 20* | 60 | 120 | 50 |
| 13 | 7** liquid flavour | 10 | 0 | 50 |
| 14 | 20 | 40 | 0 | 50 |
| 15 | 20 | 5 | 120 | 50 |
| 16–17 | 30 | 60 | 120 | 50 |
| 18 | 20 | 10 | 0 | 50 |
| 19 | 8*** powder | 40 | 0 | 50 |
| 20–21 | 20 | 5 | 120 | 50 |
| 22 | 20 | 10 | 120 | 50 |
| 23 | 20 | 10 | 120 | 50 |
| 24–25 | 20 | 5 | 120 | 50 |
| 26–27 | 30 | 60 | 120 | 50 |
| 28–30 | 40 | 30 | 120 | 50 |
| 31–37 | 30 | 60 | 120 | 50 |
| 38–39 | 20 | 120 | 240 | 50 |
| 40 | Wax powder 2 g | 300 | 300 | 50 |

*A sorbitol suspension with 3.5% aspartame and 7.5% acesulfame K.
**3 g menthol, 2.5 g eucalyptus oil, and 1.5 g anethol.
***A powder of freeze-dried leaves of eucalyptus.

Example 11

Coating in tilted kettles of 2 kg sugarfree chewing gum cores with peppermint oil, and menthol, and powder of air-dried leaves of peppermint.

| Sorbitol suspension Dosage No. | Amount of dosage g | Smoothing out time sec. | Drying time sec. | Number of revolutions rpm |
| --- | --- | --- | --- | --- |
| 1 | 20 | 120 | 120 | 50 |
| 2 | 20 | 90 | 120 | 50 |
| 3 | 20 | 60 | 60 | 50 |
| 4–9 | 30 | 30 | 90 | 50 |
| 10–11 | 30 | 30 | 120 | 50 |
| 12 | 20* | 60 | 120 | 50 |
| 13 | 7** mintoil | 10 | 0 | 50 |
| 14 | 20 | 40 | 0 | 50 |
| 15–16 | 20 | 5 | 120 | 50 |
| 17–18 | 30 | 60 | 120 | 50 |
| 19 | 20 | 10 | 0 | 50 |
| 20 | 15*** powder | 40 | 0 | 50 |
| 21–22 | 20 | 5 | 120 | 50 |
| 23–24 | 30 | 60 | 120 | 50 |
| 25–28 | 40 | 30 | 120 | 50 |
| 29–35 | 30 | 66 | 120 | 50 |
| 36–37 | 20 | 120 | 240 | 50 |
| 38 | Wax powder 2g | 300 | 300 | 50 |

*A sorbitol suspension with 2.5% aspartame.
**6 g peppermint oil and 1 g menthol.
***A powder of air-dried leaves of peppermint.

Example 12

Coating in tilted kettles of 2 kg sugar-free chewing gum cores with a mixture of liquid spearmint oil, peppermint oil, and menthol, and a mixture of powders freeze-dried leaves of peppermint and spearmint.

| Sorbitol suspension Dosage No. | Amount of dosage g | Smoothing out time sec. | Drying time sec. | Number of revolutions rpm |
| --- | --- | --- | --- | --- |
| 1 | 20 | 120 | 120 | 50 |
| 2 | 20 | 90 | 120 | 50 |
| 3 | 20 | 60 | 60 | 50 |
| 4–9 | 30 | 30 | 90 | 50 |
| 10–11 | 30 | 30 | 120 | 50 |
| 12 | 20* | 60 | 120 | 50 |
| 13 | 20 | 10 | 0 | 50 |
| 14 | 13** powder | 40 | 0 | 50 |
| 15–16 | 20 | 5 | 120 | 50 |
| 17–18 | 30 | 60 | 120 | 50 |
| 19 | 7.4*** mintoil | 10 | 0 | 50 |
| 20 | 20 | 40 | 0 | 50 |
| 21–22 | 20 | 5 | 120 | 50 |
| 23–24 | 30 | 60 | 120 | 50 |
| 25–28 | 40 | 30 | 120 | 50 |
| 29–35 | 30 | 60 | 120 | 50 |
| 36–37 | 20 | 120 | 240 | 50 |
| 38 | wax powder 2 g | 300 | 300 | 50 |

*A sorbitol suspension with 2.5% aspartame.
**8 g freeze-dried spearmint, and 5 g freeze-dried peppermint.
***3.2 g spearmint oil, 3.7 g peppermint oil, and 0.5 g menthol

Further Examples of Chewing Gum Bases

Preparation of a chewing gum base suitable for an ordinary chewing gum:

| | |
| --- | --- |
| Synthetic elastomer | 15% |
| PVA | 22% |
| Elastomer plasticizer | 26% |
| Sucrose ester | 3% |
| Filler | 14% |
| Softeners | 20% |

Preparation of a chewing gum base suitable for a chewing gum comprising an active ingredient:

| | |
| --- | --- |
| Elastomers | 4 weight-% |
| Terpene resin | 28 weight-% |
| Low molecular weight PVA | 29 weight-% |
| Emulsifier | 6 weight-% |
| Sucrose ester | 2 weight-% |
| Waxes | 31 weight-% |

The elastomer is ground in a conventional mixer for the preparation of chewing gum and gum base while being heated to 110–1 30° C. and terpene resin and low molecular weight PVA are added slowly in small portions. Finally waxes and emulsifier are added. To ensure a homogenous base it is important that all the ingredients are added in small portions and that the subsequent portions are not added until the preceding portion is ground.

Further Examples of the Preparation of a Chewing Gum

Examples of a chewing gum prepared according to the present invention:

Basic Formulation 1 comprising an active ingredient.

| | |
|---|---|
| Gum base | 35 weight-% |
| Sorbitol powder | 10 weight-% |
| Hydrogenated glucose syrup | 10 weight-% |
| Active agent if desired | 0.01–30 weight-% |
| Solubilizer | 0–20 weight-% |
| Optional flavour | 1.9 weight-% |
| Optional additional sorbitol powder q.s. | 100 weight-% |

The chewing gum pieces are prepared in the manner conventional for the preparation of chewing gum and using a conventional apparatus for the preparation of chewing gum.

The chewing gum base is melted or ground in a conventional chewing gum mixer. When the chewing gum base is homogenous, the other ingredients are admixed one by one in the order mentioned. A possible active agent may be admixed separately or in the form of a pre-mixture or in a solution. Depending on the state of the ingredients and their melting point, such pre-mixture may be a simple mixture of two or more powders, a mixture of one or more powders in one or more liquids or a mixture of more liquids at ordinary, increased or lower temperature. To ensure a good dispersion of the ingredients it may, especially when adding very small quantities of one or more of the components of the pre-mixture, be an advantage to add these as a liquid mixture or a solution where this is possible.

Further Examples of Chewing Gum Comprising Dried Fruit Powder

Example 13
Sugar-containing Chewing Gum (Standard Without Fruit Powder)

| | % |
|---|---|
| Sugar | 62.7 |
| Gum base | 25 |
| Glucose syrup | 9 |
| Citric acid | 1 |
| Sorbitol liquid 70% | 1 |
| Black current flavour | 0.9 |
| Lecithin | 0.3 |
| Triacetin | 0.1 |

Example 14
Sugar-containing Chewing Gum (with Fruit Powder and Flavour)

| | % |
|---|---|
| Sugar | 58.5 |
| Gum base | 25 |
| Glucose syrup | 10 |
| Black current powder* | 3 |
| Citric acid | 0.9 |
| Sorbitol liquid 70% | 1.5 |
| Black current flavour | 0.4 |
| Triacetin | 0.4 |
| Lecithin | 0.3 |

*freeze-dried black current

Example 15
Sugar-containing Chewing Gum (with Fruit Powder Only)

| | % |
|---|---|
| Sugar | 55.1 |
| Gum base | 25 |
| Glucose syrup | 11 |
| Black current powder* | 5 |
| Sorbitol liquid 70% | 2 |
| Citric acid | 0.8 |
| Triacetin | 0.8 |
| Lecithin | 0.3 |

*freeze-dried black current

Example 16
Sugar-containing Bubble Gum (with Fruit Powder and Flavour)

| | % |
|---|---|
| Sugar | 39.2 |
| Bubble Gum Base | 21 |
| Dextrose | 19 |
| Glucose syrup | 15 |
| Strawberry powder* | 3 |
| Sorbitol liquid 70%f | 1 |
| Citric acid | 0.8 |
| Strawberry flavour | 0.4 |
| Triacetin | 0.4 |
| Lecithin | 0.2 |

*freeze-dried strawberry

Example 17
Sugar-containing Bubble Gum (with Fruit Powder)

| | % |
|---|---|
| Sugar | 35.7 |
| Bubble Gum Base | 21 |
| Dextrose | 19 |
| Glucose syrup | 16 |
| Strawberry powder* | 5 |
| Sorbitol liquid 70% | 1.5 |
| Citric acid | 0.8 |
| Triacetin | 0.8 |
| Lecithin | 0.2 |

*50% freeze-dried and 50% tumble dried? strawberry

Example 18
Sugar Free Chewing Gum (Standard with Fruit Flavour)

| | % |
|---|---|
| Sorbitol powder | 45.6 |
| Gum base | 38 |
| Xylitol | 7 |
| Maltitol (syrup) | 5 |
| Raspberry flavour | 2 |
| Citric acid | 1 |

-continued

|  | % |
|---|---|
| Malic acid | 0.6 |
| Aspartame | 0.5 |
| Lecithin | 0.3 |

Example 19
Sugar Free Chewing Gum (with Fruit Powder and Flavour)

|  | % |
|---|---|
| Sorbitol powder | 41.7 |
| Gum base | 38 |
| Xylitol | 7 |
| Maltitol (syrup) | 6 |
| Raspberry powder* | 3 |
| Raspberry flavour | 1 |
| Citric acid | 1 |
| Triacetin | 0.9 |
| Malic acid | 0.6 |
| Aspartame | 0.5 |
| Lecithin | 0.3 |

*freeze-dried raspberry

Example 20
Sugar Free Chewing Gum (with Fruit Powder Only)

|  | % |
|---|---|
| Sorbitol powder | 37.8 |
| Gum base | 38 |
| Xylitol | 7 |
| Maltitol (syrup) | 7 |
| Raspberry powder* | 6 |
| Triacetin | 1.8 |
| Citric acid | 1 |
| Malic acid | 0.6 |
| Aspartame | 0.5 |
| Lecithin | 0.3 |

*freeze-dried raspberry

Example 21
Sugar Free Bubble Gum (with Fruit Powder and Flavour)

|  | % |
|---|---|
| Sorbitol | 54.3 |
| Bubble Gum Base | 26 |
| Sorbitol liquid 70% | 10 |
| Mannitol | 4 |
| Orange powder* | 2 |
| Lemon powder** | 1 |
| Lecithin | 1 |
| Glycerol | 0.8 |
| Citric acid | 0.5 |
| Malic acid | 0.5 |
| Orange Flavour | 0.5 |
| Lemon Flavour | 0.3 |
| Saccharin | 0.1 |

*spray dried orange juice
**freeze-dried lemon

Example 22
Sugar Free Bubble Gum (with Fruit Powder)

|  | % |
|---|---|
| Sorbitol | 51.1 |
| Bubble Gum Base | 26 |
| Sorbitol liquid 70% | 10 |
| Mannitol | 4 |
| Orange powder* | 4 |
| Lemon powder** | 2 |
| Lecithin | 1 |
| Glycerol | 0.8 |
| Citric acid | 0.5 |
| Malic acid | 0.5 |
| Saccharin | 0.1 |

*spray dried orange juice
**freeze-dried lemon

Examples of Coating of Chewing Gum by Use of Fruit Preparations

Coated chewing gum is prepared by coating a chewing gum core? with a number of coating layers. The coating most frequently takes place in rotating coating kettles in which chewing gum cores are put in motion and coating suspension? is added in small doses that are dispersed evenly on the surfaces of the cores. Subsequently, the coated cores are dried by means of air. These coating operations can be made up to 90 times until a desired coating thickness is obtained.

The coating suspension is often an aqueous solution of a sugar or the like applied at a high temperature in order to facilitate the coating process. To give a quick flavour release one or more flavouring agents according to the present invention may be applied to the chewing gum between the application of the coating suspension.

Example A
Sugar-containing Coating

|  | % |
|---|---|
| Syrup (70%) | 91 |
| Black current* | 3 |
| Water | 4.7 |
| Gelatine | 0.8 |
| Black current flavour** | 0.5 |

*Black current freeze-dried is blended with sugar suspension and is added in few or more applications
**Black current flavour is added in between the applications of coating suspension

Example B
Sugar-containing Coating (with Fruit Concentrate)

|  | % |
|---|---|
| Syrup (70%) | 88.5 |
| Black current concentrate Brix 65.3* | 3 |
| Black current freeze-dried** | 3 |

-continued

|  | % |
|---|---|
| Water | 4.7 |
| Gelatine | 0.8 |

*Black current concentrate is blended with sugar suspension and is added in few or more applications
**The freeze-dried black current powder is also blended with the sugar suspension.

Example C
Sugar Free Sorbitol Coating (with Fruit Powder and Flavour)

|  | % |
|---|---|
| Sorbitol liquid/neosorb 70/02 | 97 |
| Water | 1.5 |
| Strawberry powder* | 1 |
| Strawberry flavour** | 0.5 |

*The cores are sprinkled with strawberry powder in between the applications of sorbitol suspension
**Strawberry flavour is dosed in between the applications of sorbitol suspension Example D
Sugar Free Xylitol Coating (with Fruit Powder)

|  | % |
|---|---|
| Xylitol | 64.9 |
| 20 Water | 31.5 |
| Gelatine | 1.6 |
| Strawberry powder* | 2 |

*in between the applications of xylitol suspension the cores are sprinkled with strawberry powder (freeze-dried)

The following test profiles demonstrates the surprising effect with respect to taste which is obtained by use of the natural flavouring agent according to the invention.

Test Profile 1
Products:
1. 5573-23 Standard
Comprising 2% strawberry flavour (Wild Strawberry commercially available from the Silesia) by weight of chewing gum formulation. Dragee/coating 1.08% strawberry flavour.
2. 5553-21 Test Product
Natural vegetable flavouring agent: 1.5% Strawberry (freeze-dried powder), 1.5% Raspberry (freeze-dried powder) by weight of chewing gum formulation; dragee 0.5% strawberry freeze-dried powder) (water content of freeze-dried powder 2–6%)

Assessors:
8 persons

Time Consumption:
1 hour an assessor+time of the head of panel=18 hours.

Procedure:
This sensory analysis is tested in DANDY's Sensory Laboratory, which consists of 10 individual tasting booths according to ISO 8589. The products are served at room temperature in 40 ml tasteless plastic cups coded with a randomised three-figure number.

The products are tested at the following intervals:
Initial phase: 01 min.
Intermediate phase 1: 1–2 min.
Intermediate phase 2: 3–4 min.
End phase: 5–6 min.

There is a three-minute interval between every product being tasted. Every test is repeated. The FIZZ (French Bio System) was used to collect and calculate data.

|  | Significance clear | Significance diverse |
|---|---|---|
|  | Initial Phase | |
| Initial softness | ** | ** |
| Flavour impact | NS | NS |
| Flavour intensity | NS | NS |
| Juicy | NS | NS |
| Sourness | NS | NS |
| Sweetness | NS | NS |
| Strawberry center | *** | (7.2)* |
| Perfumed | *** | (24.0)** |
| Synthetic | *** | (36.1)*** |
| Strawberry | *** | (38.7)*** |
| Forest fruit | *** | *** |
| Astringent | * | * |
| Creaky | NS | NS |
| Volume | NS | NS |
|  | Intermediate Phase I | |
| Softness | * | * |
| Flavour intensity | NS | NS |
| Juicy | * | (2,2) NS |
| Sourness | NS | NS |
| Sweetness | NS | NS |
| Strawberry center | *** | *** |
| Perfumed | *** | (26.4)** |
| Synthetic | *** | *** |
| Strawberry | *** | (27.3)** |
| Forest fruit | *** | (23.1)** |
| Astringent | *** | *** |
| Creaky | ** | (4.3) NS |
| Volume | NS | NS |
|  | Intermediate Phase II | |
| Softness | ** | (3.0) |
| Flavour intensity | NS | NS |
| Juicy | ** | (3,2) NS |
| Sourness | NS | NS |
| Sweetness | NS | NS |
| Strawberry center | *** | (22.2)** |
| Perfumed | *** | (19.9)** |
| Synthetic | *** | (20.7)** |
| Strawberry | *** | (19.7)** |
| Forest fruit | *** | *** |
| Astringent | ** | ** |
| Creaky | *** | (4.2) NS |
| Volume | NS | NS |

Conclusion:
The difference between the two products is mainly found in the attributes: strawberry center, perfumed, synthetic, and strawberry, forest fruit and astringent.

The sample 5553-21 is found as being significantly less perfumed, synthetic and astringent than the standard 5573-23P.

The standard 5573-23P has significantly less strawberry centers, less strawberry flavour but more forest fruit flavour than the sample 5553-21.

In the end phase the sample 5553-21 is being judged as significantly higher in flavour intensity than the sample.

In the initial phase, the standard is significantly softer than 5553-21. This is also the case in the initial phase I, but riot in the rest of the profile, where the two products are alike concerning the texture.

Test Profile 2
Products:
1. 5553-46 Standard

Comprising 0.6% raspberry flavour, 0.6% orange flavour, 0.9% strawberry on the chewing gum formulation, 0.5% raspberry flavour in the dragee/coating.

2. 5553-42 Test Product

Comprising 1% raspberry, 1% orange, 1% strawberry freeze-dried powders. 2% raspberry powder freeze-dried in the dragee/coating.

Assessors:
  10 persons

Time Consumption:
  1 hour an assessor+time of the head of panel=18 hours.

Procedure:
As Test Profile 1

|  | Significance clear | Significance diverse |
|---|---|---|
| *Initial Phase* | | |
| Initial softness | * | * |
| Flavour impact | *** | (3.1) NS |
| Flavour intensity | NS | NS |
| Juicy | NS | NS |
| Sourness | ** | ** |
| Sweetness | NS | NS |
| Synthetic | *** | (35.9)*** |
| Red fruit | *** | (8.5)* |
| Orange fruit | *** | (4.2) NS |
| Softness | *** | *** |
| Astringent | * | * |
| Creaky | NS | NS |
| Volume | NS | NS |
| *Intermediate Phase I* | | |
| Softness | *** | *** |
| Flavour intensity | ** | ** |
| Juicy | *** | *** |
| Sourness | NS | NS |
| Sweetness | NS | NS |
| Synthetic | *** | (25.4)*** |
| Red fruit | *** | (7.8)* |
| Orange fruit | *** | (3.8) NS |
| Softness | ** | ** |
| Astringent | ** | ** |
| Creaky | *** | (3.3) NS |
| Volume | ** | ** |
| *Intermediate Phase II* | | |
| Softness | ** | (2.8) NS |
| Flavour intensity | * | * |
| Juicy | * | * |
| Sourness | NS | NS |
| Sweetness | NS | NS |
| Synthetic | *** | *** |
| Red fruit | *** | *** |
| Orange fruit | ** | (3.2) NS |
| Softness | ** | (4.5) NS |
| Astringent | ** | ** |
| Creaky | *** | (4.7) NS |
| Volume | ** | ** |
| *End Phase* | | |
| Softness | NS | NS |
| Flavour intensity | NS | NS |
| Juicy | * | (2.5) NS |
| Sourness | NS | NS |
| Sweetness | NS | NS |
| Synthetic | *** | (20.6)* |
| Red fruit | *** | *** |
| Orange fruit | ** | (2.3) NS |
| Softness | *** | (3.4) NS |
| Astringent | NS | NS |
| Creaky | ** | (2.0) NS |
| Volume | *** | (6.4)* |

Conclusion:

In the beginning of the profile the standard is significantly softer that the trial.

All through the profile, the standard is judged as being significantly more synthetic than the trial, and significantly less red fruit that the trial 5553-42.

The standard is also more astringent in three of the four phases than the trial, and in the three last phases the trial is significantly bigger in volume than the standard.

In the two intermediate phases the trial 5553-42 is significantly more juicy and has a higher flavour intensity than the standard.

Test Profile 3
Products:
1. 5553-45 Standard

Comprising 0.7% lemon, 1.2% orange and 0.10% pink grape flavours in the chewing gum formulation and in the coating/drage 0.1% lemon, 0.2% orange, 0.05% pink grape flavours.

2. 5553-38 Test Product

Comprising 0.7% orange flavour and 0.1% pink grape, 2% % freeze-dried orange powder, 1.5% % freeze-dried lemon powder in the chewing gum formulation and 0.7% freeze-dried orange powder in the coating.

Assessors:
  10 persons

Time Consumption:
  1 hour an assessor+time of the head of panel=18 hours

Procedure:
As Test Profile 1

|  | Significance clear | Significance diverse |
|---|---|---|
| *Initial Phase* | | |
| Initial softness | * | * |
| Flavour impact | *** | *** |
| Flavour intensity | ** | (3.3) NS |
| Juicy | NS | NS |
| Sourness | NS | NS |
| Sweetness | NS | NS |
| Synthetic | ** | ** |
| Red fruit | NS | NS |
| Orange fruit | *** | (72.8)*** |
| Softness | *** | (50.3)*** |
| Astringent | NS | NS |
| Creaky | NS | NS |
| Volume | *** | *** |
| *Intermediate Phase I* | | |
| Softness | *** | *** |
| Flavour intensity | NS | NS |
| Juicy | NS | NS |
| Sourness | *** | (4.6) NS |
| Sweetness | ** | * |
| Citrus | NS | NS |
| Synthetic | NS | NS |
| Softness | *** | *** |
| Cheesiness | *** | *** |
| Astringent | NS | NS |
| Creaky | NS | NS |
| Volume | *** | (17.4)*** |

-continued

|  | Significance clear | Significance diverse |
|---|---|---|
| Intermediate Phase II | | |
| Softness | *** | *** |
| Flavour intensity | NS | (3.0) NS |
| Juicy | NS | NS |
| Sourness | ** | ** |
| Sweetness | NS | NS |
| Citrus | NS | NS |
| Synthetic | NS | NS |
| Softness | *** | *** |
| Cheesiness | *** | *** |
| Astringent | NS | NS |
| Creaky | * | (0.7) NS |
| Volume | *** | (12.8)** |
| End Phase | | |
| Softness | *** | *** |
| Flavour intensity | NS | |
| Juicy | NS | |
| Sourness | * | * |
| Sweetness | NS | |
| Citrus | NS | |
| Synthetic | NS | |
| Softness | *** | *** |
| Cheesiness | *** | (17.3)** |
| Astringent | NS | NS |
| Creaky | ** | (1.2) NS |
| Volume | *** | (24.5)*** |

Conclusion:

Concerning the texture, the standard in all four phases is significantly softer and more cheesy than the trial. It is known that a softer product releases the taste faster than a harder product. Accordingly, the chosen standard formulation is more likely to release the flavour in the initial phase corresponding to the finding that the rest in the end phase demonstrate increased impact, flavour intensity, sourness and a juicy taste.

Sourness is an indicator of freshness. Despite the harder product, the decreased synthetic taste clearly seen in the test profile 1 and 2, is also indicated in the present profile even though it is only in the coating that the natural lemon powder is present.

Furthermore, preliminary test by use of natural freeze-dried mint, spearmint, and eucalyptus in the coating has resulted in increased taste sensation compared with use of ordinary flavour components.

What is claimed is:

1. A chewing gum comprising:
   a) a gum base material;
   b) a water soluble portion;
   c) a coating comprising a flavouring agent wherein at least 10% by weight of the flavouring agent is a natural vegetable flavouring agent comprising cellular material from a plant.

2. A chewing gum according to claim 1 wherein at least 20% by weight of the flavouring agent in the coating is a natural vegetable flavouring agent comprising cellular material from a plant.

3. A chewing gum according to claim 1 wherein at least 70% by weight of the flavouring agent in the coating is a natural vegetable flavouring agent comprising cellular material from a plant.

4. A chewing gum according to claim 1 wherein at least 95% by weight of the flavouring agent in the coating is a natural vegetable flavouring agent comprising cellular material from a plant.

5. A chewing gum according to claim 1 wherein the natural vegetable flavouring agent comprising cellular material from a plant in the coating comprises a fruit or one or more herbs.

6. A chewing gum according to claim 1 wherein the natural vegetable flavouring agent in the coating includes coconut, grape fruit, orange, lime, lemon, mandarin, pineapple, strawberry, raspberry, mango, passion fruit, kiwi, apple, pear, peach, apricot, cherry, grapes, banana, cranberry, blueberry, black currant, red currant, gooseberry, lingon berries, thyme, basil, camille, valerian, fennel, parsley, camomile, tarragon, lavender, dill, cumin, bergamot, salvia, aloe vera balsam, spearmint, peppermint, eucalyptus or mixtures thereof.

7. A chewing gum according to claim 1 wherein the water content of the natural flavouring agent in the coating is less than 75% by weight.

8. A chewing gum according to claim 1 wherein the water content of the natural flavouring agent in the coating is less than 20% by weight.

9. A chewing gum according to claim 1 wherein the natural flavouring agent in the coating is freeze-dried.

10. A chewing gum according to claim 1 wherein the natural flavouring agent in the coating is in the form of a powder, slices or pieces or combinations thereof.

11. A chewing gum according to claim 10 wherein the natural flavouring agent in the coating has a particle size of less than 3 mm, determined on the longest dimension of the particle.

12. A chewing gum according to claim 11 wherein the natural flavouring agent in the coating has a particle size of about 3 μm to 2 mm.

13. A chewing gum according to claim 1 wherein the natural flavouring agent in the coating is substantially intact seeds from a fruit.

14. A chewing gum according to claim 13 wherein said seeds are from a fruit including strawberry, blackberry or raspberry.

15. A chewing gum according to claim 1 wherein the natural vegetable flavouring agent in the coating also provides the chewing gum with a natural colour.

16. A chewing gum according to claim 1 wherein the natural flavouring agent is used in the coating of the chewing gum and in a chewing gum core.

17. A chewing gum according to claim 16 wherein the natural flavouring agent in the coating of the chewing gum and in the chewing gum core provides a natural colour to the chewing gum core.

18. A chewing gum according to claim 1 wherein the natural flavouring agent in the coating provides the chewing gum with a basic colour.

19. A chewing gum according to claim 18 wherein the natural flavouring agent in the coating provides the chewing gum with a basic colour as well as more intense colour spots.

20. A chewing gum according to claim 1 comprising from 5% to 85% by weight of a gum base material.

21. A chewing gum according to claim 1 comprising one or more of the following: at least one softener; a bulk sweetener; a high intensity sweetener; an emulsifier, an elastomer plasticizer; an elastomer; a mono-diglyceride; a sucrose fatty acid ester.

22. A method for preparing a chewing gum composition comprising providing a mixture of:
   a) a gum base material; and
   b) a water soluble portion;
forming chewing gum pieces and coating the chewing gum pieces with a coating comprising a flavouring agent wherein at least 10% by weight of the flavouring agent is a natural vegetable flavouring agent comprising cellular material from a plant.

23. A method according to claim 22 wherein at least 20% by weight of the flavouring agent in the coating is a natural vegetable flavouring agent comprising cellular material from a plant.

24. A method according to claim 22 wherein at least 30% by weight of the flavouring agent in the coating is a natural vegetable flavouring agent comprising cellular material from a plant.

25. A method according to claim 22 wherein at least 40% by weight of the flavouring agent in the coating is a natural vegetable flavouring agent comprising cellular material from a plant.

26. A method according to claim 22 wherein the natural vegetable flavouring agent in the coating comprises one or more fruits or one or more herbs.

27. A method according to claim 22 wherein the natural vegetable flavouring agent in the coating includes coconut, grape fruit, orange, lime, lemon, mandarin, pineapple, strawberry, raspberry, mango, passion fruit, kiwi, apple, pear, peach, apricot, cherry, grapes, banana, cranberry, blueberry, black currant, red currant, gooseberry, lingon berries, thyme, basil, camille, valerian, fennel, parsley, camomile, tarragon, lavender, dill, cumin, bargamot, salvia, aloe vera balsam, spearmint, peppermint, eucalyptus or mixtures thereof.

28. A method according to claim 22 wherein the water content of the natural flavouring agent in the coating is less than 75% by weight.

29. A method according to claim 22 wherein the water content of the natural flavouring agent in the coating is less than 20% by weight.

30. A method according to claim 22 wherein the natural flavouring agent in the coating is freeze-dried.

31. A method according to claim 22 wherein the natural flavouring agent in the coating is in the form of a powder, slices or pieces or combinations thereof.

32. A method according to claim 31 wherein the natural flavouring agent in the coating is in a form where the particle size is less than 3 mm, such as less than 2 mm, more preferred less than 1 mm, calculated as the longest dimension of the particle.

33. A method according to claim 22 wherein the natural flavouring agent in the coating is in a form where the particle size is from about 3 $\mu$m to 2 mm.

34. A method according to claim 22 wherein the natural flavouring agent in the coating comprises substantially intact seeds from a fruit.

35. A method according to claim 34 wherein said seeds are from a fruit selected from the group consisting of strawberry, blackberry and raspberry.

36. A method according to claim 22 wherein the natural vegetable flavouring agent in the coating also provides the chewing gum with a natural colour.

37. A method according to claim 22 wherein the natural flavouring agent is also used in the chewing gum core.

38. A method according to claim 22 wherein the natural flavouring agent in the coating provides a natural colour to the coating.

39. A method according to claim 38 wherein the natural flavouring agent in the coating provides the chewing gum coating with a basic colour as well as more intense colour spots.

40. A method according to claim 22 wherein the gum base material constitutes from 5% to 85% by weight of the chewing gum.

41. A method according to claim 22 comprising adding one or more of the following ingredients to the chewing gum composition: at least one softener, a bulk sweetener; a high intensity sweetener; an emulsifier; an elastomer plasticizer; an elastomer; a monodiglyceride; or a sucrose fatty acid ester.

42. A method of coating a chewing gum comprising covering chewing gum pieces with a composition comprising cellular material from a plant.

43. A method according to claim 42 wherein the cellular material from a plant is a flavouring agent and it comprises substantially intact cellular components.

* * * * *

UNITED STATES PATENT AND TRADEMARK OFFICE
CERTIFICATE OF CORRECTION

PATENT NO. : 6,787,167 B1
DATED : September 7, 2004
INVENTOR(S) : Bronislaw-Jan Stahl It is certified that error appears in the above-identified patent and that said Letters Patent is hereby corrected as shown below:

Column 1,
Line 28, insert -- flavouring -- before "agent".

Column 2,
Line 3, insert a period, -- . -- after "have" and replace "initially" with -- Initially --.
Line 7, replace "compete" with -- complete --.

Column 3,
Line 11, replace "increments" with -- increment(s) --.

Column 4,
Line 16, delete the period "." after "longest".
Line 19, insert space before "to", in both occurrences.
Line 41, delete the period, "." before "filler".

Column 5,
Line 29, insert space after "esters", first occurrence.

Column 8,
Line 46, replace "palmitatetstearate" with -- palmitate/stearate --.
Line 63, replace "hexachlorophens" with -- hexachlorophene --.
Line 67, replace "Furthermore" with -- furthermore --.

Column 10,
Line 41, replace "sweeteners)" with -- sweetener(s) --.

Column 11,
Line 61, delete "all".

Column 16,
Example 8, line 21, replace "39" with -- 38 --.
Example 9, line 48, replace "17-19" with -- 17-18 --.

UNITED STATES PATENT AND TRADEMARK OFFICE
CERTIFICATE OF CORRECTION

PATENT NO.    : 6,787,167 B1
DATED         : September 7, 2004
INVENTOR(S)   : Bronislaw-Jan Stahl It is certified that error appears in the above-identified patent and that said Letters Patent is hereby corrected as shown below:

Column 17,
Example 11, line 53, replace "66" with -- 60 --.

Column 18,
Line 56, replace "1 30" with -- 130 --.

Column 23,
Example D, line 36, delete "20" before "Water".

Column 24,
Line 2, replace "01" with -- 0-1 --.
Line 65, replace "riot" with -- not --.

Column 26,
Line 61, replace "*" with -- ** --.

Signed and Sealed this

Eleventh Day of October, 2005

JON W. DUDAS
*Director of the United States Patent and Trademark Office*